United States Patent
Epstein et al.

(10) Patent No.: US 6,331,172 B1
(45) Date of Patent: Dec. 18, 2001

(54) APPLICATOR FOR DISPENSING MEASURED QUANTITIES WITH USE OF CONTROLLED SUCTION

(75) Inventors: Gordon Howard Epstein, Fremont; Alan Plyley; Russell James Redmond, both of Goleta, all of CA (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 08/838,078

(22) Filed: Apr. 14, 1997

(51) Int. Cl.[7] .................................................. A61M 37/00
(52) U.S. Cl. .............................................. 604/82; 604/191
(58) Field of Search ................................ 604/82, 73, 94, 604/131, 135, 134, 173, 181, 187, 191, 208, 214, 218, 224, 228, 46, 49, 56; 424/423; 222/137, 327, 391; 239/113

(56) References Cited

U.S. PATENT DOCUMENTS

| | | |
|---|---|---|
| 1,889,425 | 11/1932 | Sorensen . |
| 2,158,593 | 5/1939 | Scrimgeour . |

(List continued on next page.)

FOREIGN PATENT DOCUMENTS

| | | |
|---|---|---|
| 81 33 489 U | 5/1982 | (DE) . |
| 302411 A2 | 2/1989 | (EP) . |
| 592242 A1 | 4/1994 | (EP) . |
| WO/95/31137 | 11/1995 | (WO) . |
| WO/97/28834 | 8/1997 | (WO) . |

OTHER PUBLICATIONS

PCT International Search Report, PCT/US98/07488, Jul. 8, 1998.
PCT International Search Report, PCT/US98/07846, Jul. 18, 1998.

(List continued on next page.)

*Primary Examiner*—Richard K. Seidel
*Assistant Examiner*—LoAn H. Thanh
(74) *Attorney, Agent, or Firm*—Handal & Morofsky; Oppenheimer, Wolff & Donnelley

(57) ABSTRACT

A medical fluid applicator for dispensing a fluid onto biological tissues in tissue adhesive or sealant applications includes a dispensing pathway with an audible loudness indicator that signals the cumulative amount of fluid delivered by varying the pitch or tone of audible signals emitted at discrete volumetric increments. A suction pathway is also included for applying vacuum pressure to the applicator tip contemporaneous with the fluid application. The medical fluid applicator further includes a clearing pathway for retrogradedly withdrawing coagulated mixed fluids, such as mixed two-part tissue adhesives, from the applicator tip. A valve manifold and a shuttle valve are actuated to adjust the operation of vacuum pressure in the device between the various suctioning, clearing, and venting conduits of the device. The valve manifold is also adapted to couple a vent pathway and the suction pathway simultaneously to the vacuum conduit adapted for connection to a vacuum source. The coupling of vacuum to these pathways may be selectively adjusted by use of inversely and reciprocally shaped valving apertures on the valve manifold, such that preselected levels of applied suction at the suction pathway may be achieved. The device also includes a supply device portion and an applicator portion removably coupled thereto. The supply device portion includes the proximal portions of the dispensing assembly including the audible loudness indicator and the fluid reservoirs. The applicator portion includes the suction conduit, the clearing conduit, and a mixing conduit for mixing the components of the fluid reservoirs immediately prior to fluid delivery. A filling dispenser is further provided which is keyed to engage the supply device portion of the device in a predetermined orientation such that each fluid reservoir of the supply device is coupled for filling from a specified, predetermined filling reservoir.

59 Claims, 21 Drawing Sheets

U.S. PATENT DOCUMENTS

| | | |
|---|---|---|
| 2,576,766 | 11/1951 | Sokolik . |
| 2,812,765 | 11/1957 | Tofflemire . |
| 3,065,749 | 11/1962 | Brass . |
| 3,071,402 | 1/1963 | Lasto . |
| 3,159,312 | 12/1964 | Van Sciver, II . |
| 3,179,107 | 4/1965 | Clark . |
| 3,188,056 | 6/1965 | Trumbull . |
| 3,208,145 | 9/1965 | Turner . |
| 3,469,582 | 9/1969 | Jackson . |
| 3,626,928 | 12/1971 | Barringer . |
| 3,767,085 | 10/1973 | Cannon . |
| 3,828,980 | 8/1974 | Creighton . |
| 3,949,748 | 4/1976 | Malmin . |
| 4,040,420 | 8/1977 | Speer . |
| 4,043,042 | 8/1977 | Perfect . |
| 4,067,479 | 1/1978 | Moline . |
| 4,109,653 | 8/1978 | Kozam . |
| 4,193,406 | 3/1980 | Jinotti . |
| 4,223,676 | 9/1980 | Wuchinich . |
| 4,266,545 | 5/1981 | Moss . |
| 4,270,525 | 6/1981 | Furihata . |
| 4,294,251 | 10/1981 | Greenwald . |
| 4,299,221 | 11/1981 | Phillips . |
| 4,325,913 | 4/1982 | Wardlaw . |
| 4,359,049 | 11/1982 | Redl et al. . |
| 4,397,640 | 8/1983 | Haug et al. . |
| 4,445,517 | 5/1984 | Feild . |
| 4,519,385 | 5/1985 | Atkinson . |
| 4,573,979 | 3/1986 | Blake . |
| 4,617,013 | 10/1986 | Betz . |
| 4,629,455 | 12/1986 | Kanno . |
| 4,631,055 | 12/1986 | Redl et al. . |
| 4,696,669 | 9/1987 | Menhusen . |
| 4,708,717 | 11/1987 | Deane et al. . |
| 4,735,616 | 4/1988 | Eibl et al. . |
| 4,743,229 | 5/1988 | Chu . |
| 4,759,349 | 7/1988 | Betz . |
| 4,776,840 * | 10/1988 | Freitas et al. ............... 604/33 |
| 4,842,581 | 6/1989 | Davis . |
| 4,857,047 | 8/1989 | Amoils . |
| 4,874,368 | 10/1989 | Miller et al. . |
| 4,891,044 | 1/1990 | Mitchell . |
| 4,904,238 | 2/1990 | Williams . |
| 4,925,447 | 5/1990 | Rosenblatt . |
| 4,935,006 | 6/1990 | Hasson . |
| 4,941,872 | 7/1990 | Felix . |
| 4,969,669 | 11/1990 | Sauer . |
| 4,978,336 | 12/1990 | Capozzi et al. . |
| 4,979,942 | 12/1990 | Wolf et al. . |
| 4,981,473 | 1/1991 | Rosenblatt . |
| 5,024,615 | 6/1991 | Buechel . |
| 5,024,654 | 6/1991 | Tyler . |
| 5,045,055 | 9/1991 | Gonser . |
| 5,049,135 | 9/1991 | Davis . |
| 5,061,180 | 10/1991 | Wiele . |
| 5,116,315 | 5/1992 | Capozzi et al. . |
| 5,120,305 | 6/1992 | Boehringer . |
| 5,145,367 | 9/1992 | Kasten . |
| 5,163,433 | 11/1992 | Kagawa . |
| 5,186,714 | 2/1993 | Boudreault et al. . |
| 5,217,465 | 6/1993 | Steppe . |
| 5,226,877 | 7/1993 | Epstein . |
| 5,295,956 | 3/1994 | Bales . |
| 5,300,022 | 4/1994 | Klapper et al. . |
| 5,304,165 | 4/1994 | Haber . |
| 5,314,412 | 5/1994 | Rex . |
| 5,318,782 | 6/1994 | Weis-Fogh . |
| 5,328,459 | 7/1994 | Laghi . |
| 5,348,542 | 9/1994 | Ellis . |
| 5,368,560 | 11/1994 | Rambo . |
| 5,368,563 | 11/1994 | Lonneman et al. . |
| 5,395,326 | 3/1995 | Haber et al. . |
| 5,405,607 | 4/1995 | Epstein . |
| 5,419,769 | 5/1995 | Devlin . |
| 5,447,494 | 9/1995 | Dorsey, III . |
| 5,474,540 | 12/1995 | Miller et al. . |
| 5,476,450 | 12/1995 | Ruggio . |
| 5,520,658 | 5/1996 | Holm . |
| 5,520,685 | 5/1996 | Wojciechowicz . |
| 5,571,081 | 11/1996 | Adhoute . |
| 5,584,815 | 12/1996 | Pawelka et al. . |
| 5,585,007 | 12/1996 | Antanavich . |
| 5,603,700 | 2/1997 | Daneshvar . |
| 5,605,255 | 2/1997 | Reidel et al. . |
| 5,605,541 | 2/1997 | Holm . |
| 5,612,050 | 3/1997 | Rowe et al. . |
| 5,648,265 | 7/1997 | Epstein . |
| 5,695,472 | 12/1997 | Wyrick . |
| 5,749,968 | 5/1998 | Melanson et al. . |
| 5,759,171 | 6/1998 | Coelho et al. . |
| 5,902,264 | 5/1999 | Toso . |
| 5,975,367 | 11/1999 | Coelho . |
| 5,989,215 | 11/1999 | Delmotte . |

OTHER PUBLICATIONS

U.S. application No. 08/839,614, Epstein et al., filed Apr. 14, 1997.
U.S. application No. 08/645,464, Epstein.
U.S. application No. 08/703,148, Epstein.
U.S. application No. 08/839,614, Epstein et al.
U.S. application No. 08/863,883, Epstein.
U.S. application No. 08/946,364, Epstein et al.

* cited by examiner

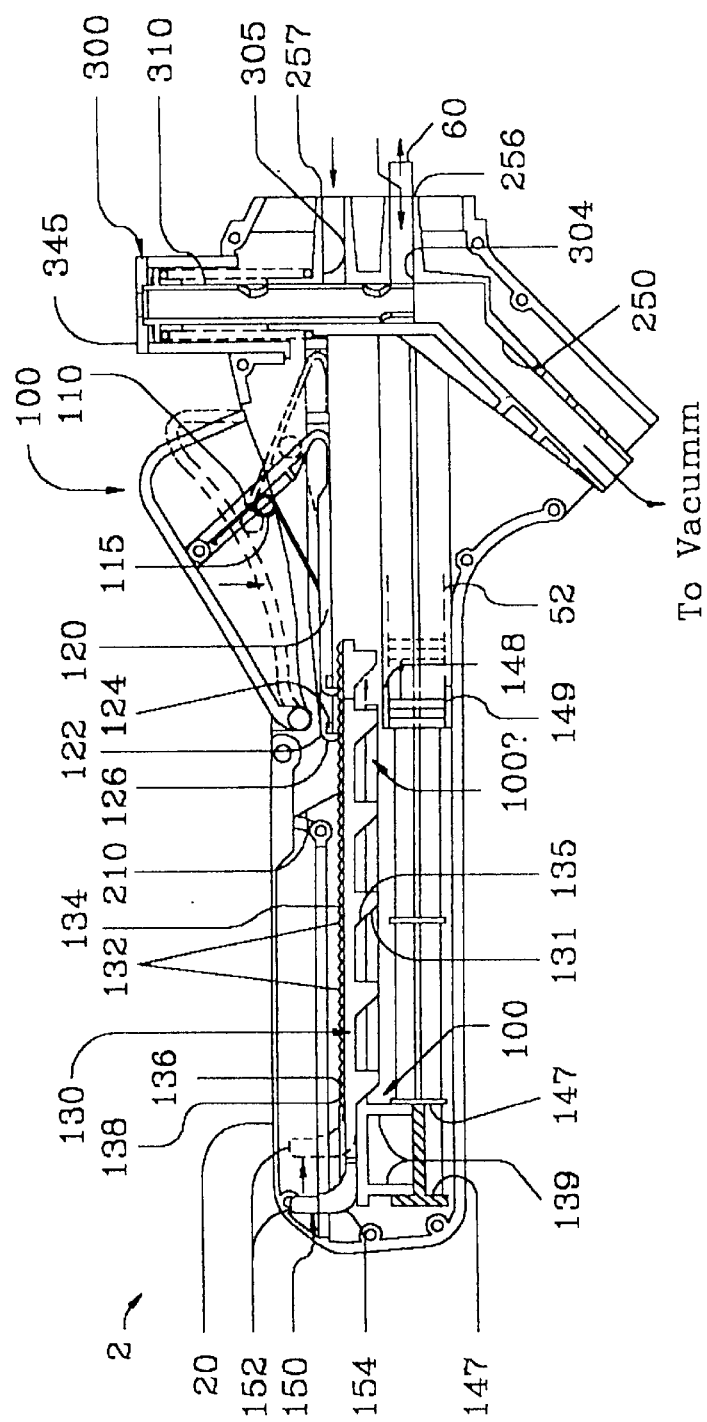
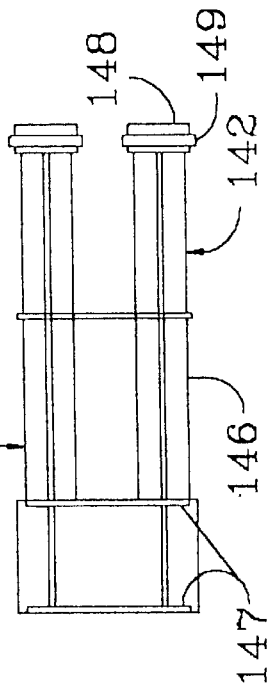
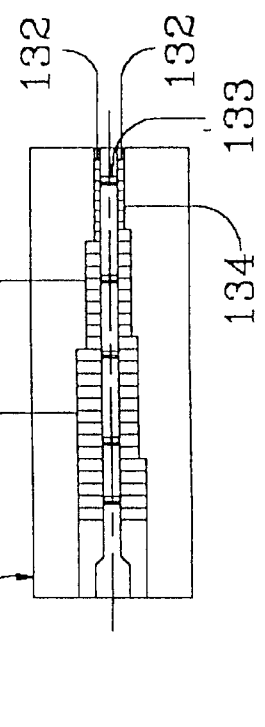
FIGURE 5
FIGURE 6
FIGURE 7

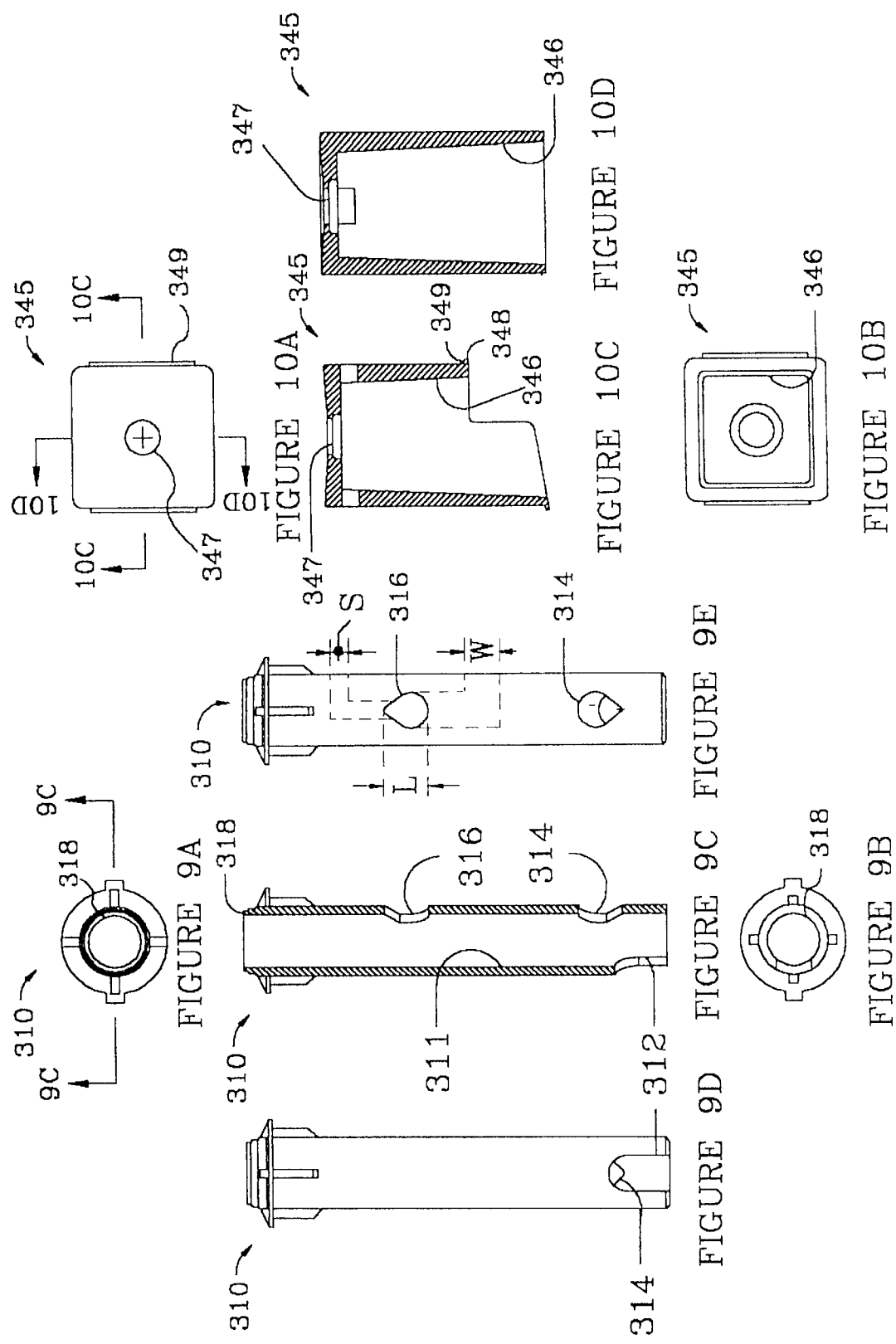

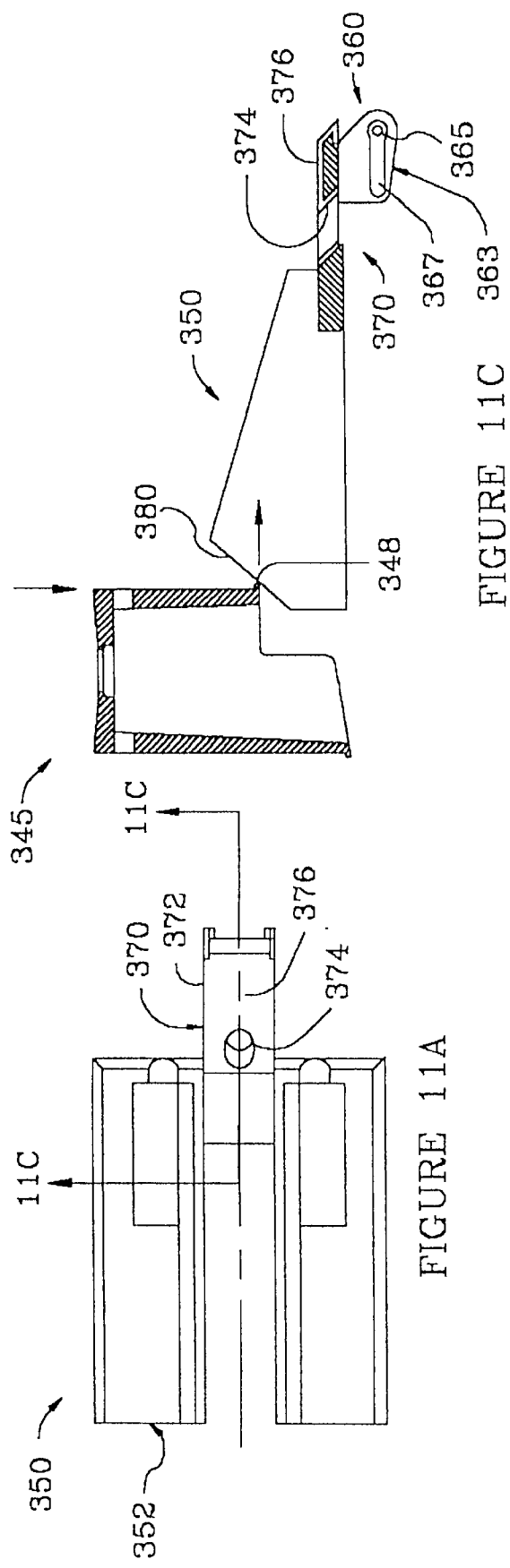
FIGURE 11C
FIGURE 11A
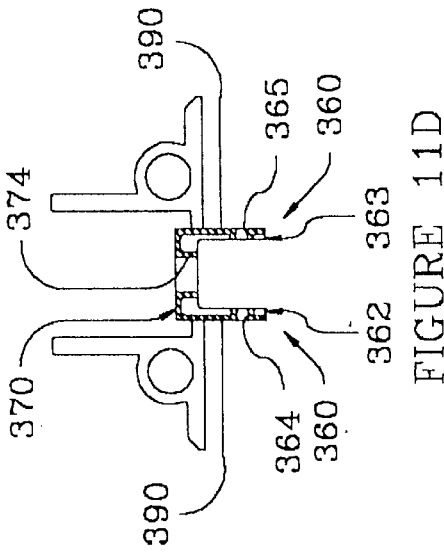
FIGURE 11D
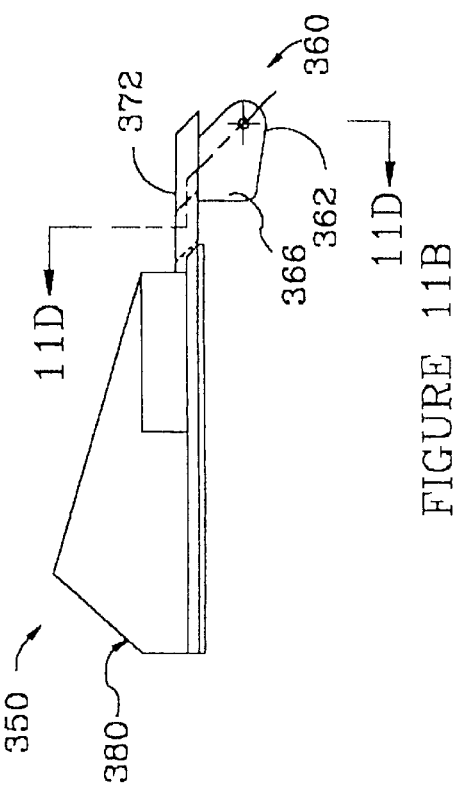
FIGURE 11B

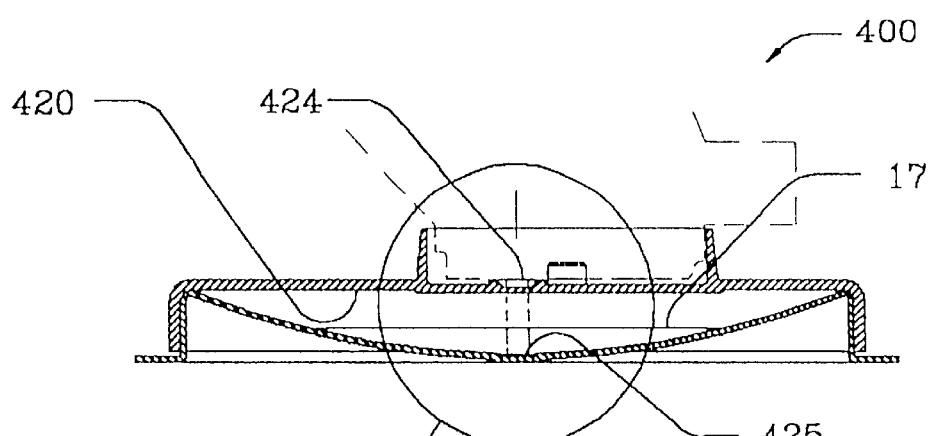
FIGURE 17B
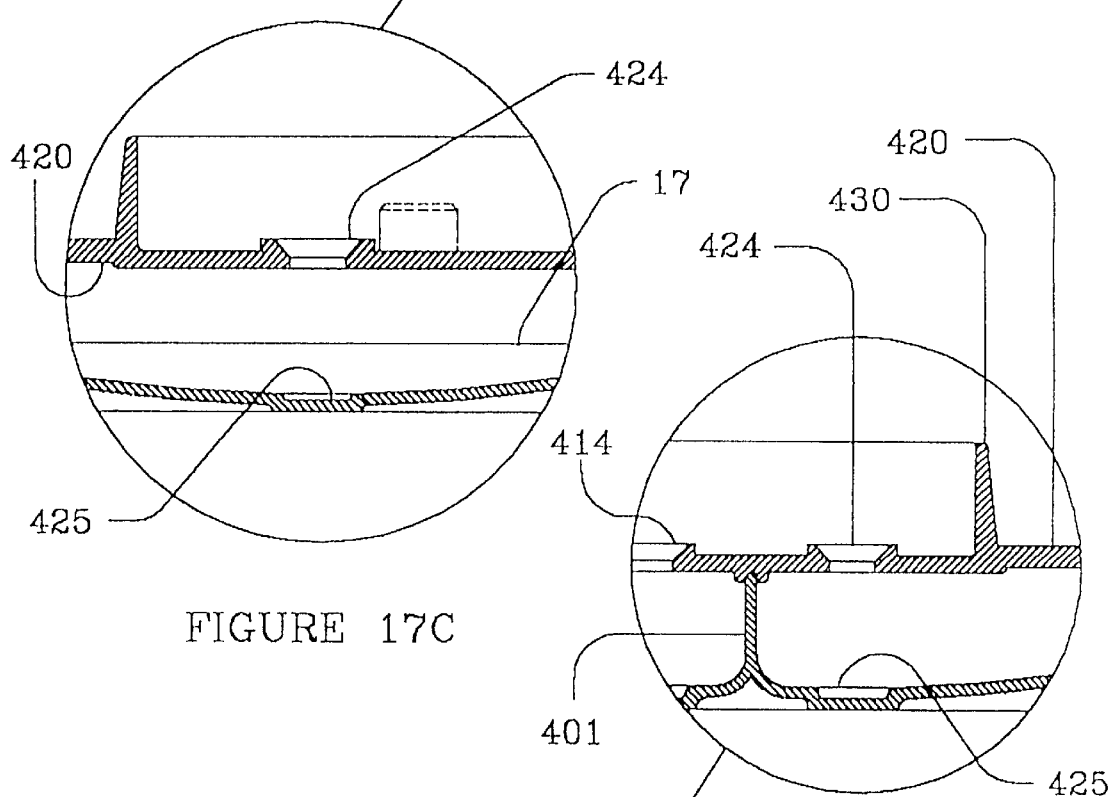
FIGURE 17C
FIGURE 17E
FIGURE 17D

APPLICATOR FOR DISPENSING MEASURED QUANTITIES WITH USE OF CONTROLLED SUCTION

TECHNICAL FIELD

The invention is a medical device which combines controlled dispensing of liquid or semiliquid substances with controlled suction. More specifically, the invention is a tissue adhesive applicator which selectively provides suction at the applicator tip during or immediately prior to adhesive application, or for clearing coagulated adhesive from the applicator tip.

BACKGROUND

Various known devices provide for the controlled dispensing of medical fluids. Furthermore, some are adapted to provide suction as well as irrigation at the dispensing tip. The suction is generally suitable for the removal of fluids during surgical procedures.

Examples of medical devices which are adapted to dispense fluid as well as provide vacuum at the working tip are disclosed in U.S. Pat. Nos.: 3,065,749; 3,469,582; 4,397,640; 4,573,979; 4,617,013; 4,696,669; 4,708,717; 4,776,840; 4,857,047; 5,061,180; and 5,226,877. Some of these devices have a suction pathway which is distinct from their dispensing pathway, such as those disclosed in U.S. Pat. Nos.: 3,065,749; 4,397,640; 4,573,979; 4,617,013; 4,696,669; 4,708,717; 4,857,047; 5,061,180; 5,226,877. Alternatively, some use the same pathway to either provide suction or dispense fluid, such as the devices disclosed in U.S. Pat. No. 3,469,582 and 4,776,840.

Referring to U.S. Pat. No. 4,776,840 to Freitas, a device is disclosed which has a suction outlet adjacent a dispensing outlet which may also provide suction in parallel to the suction outlet. In order to provide suction at the working tip, the user depresses a plunger which connects the vacuum source to the dispensing outlet pathway in addition to the suction pathway. In contrast, if the user desires to dispense fluid, the user pulls a trigger switch which is in communication with a piston. As the trigger is displaced, the piston is displaced and pushes fluid through a check valve leading to the dispensing outlet pathway.

In addition, devices adapted to dispense tissue adhesives or sealant are disclosed in U.S. Pat. Nos.: 4,040,420; 4,359,049; 4,735,616; 4,874,368; 4,978,336; 5,116,315; 5,226,877; 5,368,563; 5,474,540; and 5,605,541. Typically, these known devices have two self-contained fluid reservoirs. Each reservoir has an outlet passageway which may lead to a common passageway in which the fluids mix. In many tissue adhesive applications, a fibrinogen solution is mixed with a thrombin solution to start the clotting process and form the physiological adhesive or sealant. Often, the mixture that remains in the mixing passageway commonly causes clogging of the dispensing tip. To overcome this obstacle, some devices have been developed to spray the independent components of a two part biological adhesive so that mixing occurs in the spray between a device nozzle head and the tissue. Examples of such spraying devices are disclosed in U.S. Pat. Nos. 5,368,563 and 5,605,541.

Finally, disclosed suction and medical dispensing devices provide very limited volume indicators, such as visual volume indicators on the working device which require the user's attention to be diverted from the working area of fluid dispensing. An alternative volume indication mechanism is disclosed in U.S. Pat. No. 5,226,877 to Epstein. Epstein discloses a medical dispensing device that has an audible loudness indicator which provides discrete audible "clicks" at predetermined incremental volumes of fluid delivery. However, this beneficial indicator does not audibly indicate the cumulative volume of fluid dispensed, but instead requires a user to remember the number of clicks.

There is still a need for an audible loudness indicator which emits audible signals to a user that indicate the cumulative volume of fluid dispensed at each incremental volume of fluid delivery.

There is also still a need for an apparatus and method for withdrawing a cast of cured tissue adhesive or other congealing fluid from the dispensing conduit in the tip of a medical fluid applicator.

SUMMARY OF THE INVENTION

The present invention is a medical fluid applicator assembly which includes a dispensing assembly in combination with a suction assembly.

In one aspect of the invention, a dispensing assembly includes an audible loudness indicator which signals the cumulative volume of fluid dispensed by changing the pitch or loudness of an audible tone produced at predetermined volumetric increments.

In one variation of this fluid dispensing assembly, the audible loudness indicator includes a rack and pawl assembly which has a plurality of teeth with variably positioned regions on the rack. The varied teeth produce incremental tones with changing pitch when the various regions translate across a striker.

In another variation of this fluid dispensing assembly, each of two reservoirs contains one component of a two-part fluid to be mixed prior to delivery. The reservoirs are coupled to a common portion of a dispensing conduit in a shaped tip applicator. An actuator delivers each adhesive component from its respective reservoir, into the dispensing conduit where they are mixed, and distally out of the applicator tip. Further to this variation, one chamber preferably houses a fibrinogen-containing fluid and the other chamber houses a fluid containing a catalyst for coagulating the fibrinogen, such as a thrombin-containing fluid.

In another aspect of the invention, a medical suction device assembly includes a vacuum conduit, a suction conduit, a vent conduit, and a valve manifold adapted to adjust the fluid communication between the vacuum conduit and the suction conduit while simultaneously and inversely adjusting the proportion of vacuum applied to the vent conduit. In this arrangement a controllable range of applied vacuum at the suction conduit may be selected by varying the proportion of vacuum pressure which is applied between the vent and the suction conduit.

In one variation of this medical suction device assembly, the valve manifold is engaged within a valve housing which includes a vent port in communication with the vent conduit, a suction port in communication with the suction conduit, and a vacuum port in communication with the vacuum conduit. The valve manifold has a valve wall forming a valve chamber and which includes a vacuum aperture, a suction aperture, and a vent aperture. The suction and vent apertures are adapted such that, by varying the positioning of the valve manifold between selected positions within the valve housing, they translate across the suction port and vent port, respectively, at the same time and while the valve vacuum aperture is registered with the vacuum port.

In a further variation, each of the suction and vent apertures also has a non-uniform cross section taken along an elongate axis thereof which is aligned with the axis of motion for translating across the corresponding valve housing port. Each of these two apertures is further positioned an the valve manifold in a relatively reciprocal orientation relative to the other, such that when the valve manifold is adjusted to register an increased-diameter portion of one aperture with its corresponding port, the other aperture has a decreased-diameter portion in registry with the other corresponding port.

In another aspect of the invention, a combination dispenser/suction device assembly includes an applicator tip portion with a suction conduit and a dispensing conduit. A valve manifold is adapted to shuttle an applied vacuum source between the suction conduit and the dispensing conduit.

In another aspect of the invention, an applicator/suction device assembly includes a dispensing pathway which is coupled at one end to at least one fluid reservoir and at the other end to a dispensing conduit in an applicator tip portion of the device. The dispensing conduit terminates distally at a tip dispensing aperture. A valve manifold is adapted to selectively interrupt the dispensing pathway by isolating the fluid reservoir from the dispensing conduit, and is further adapted to fluidly couple the dispensing conduit to a vacuum conduit which is further coupled to a vacuum source.

In a further variation of this applicator/suction device assembly, the applicator tip portion also includes a suction conduit which terminates in a tip suction aperture. The valve manifold of this variation is adapted to selectively direct applied vacuum from the vacuum conduit to either of the suction or dispensing conduits in the applicator tip portion. The valve manifold is adjustable from a first position, wherein the vacuum conduit communicates with the suction conduit and is isolated from the dispensing conduit, to a second position wherein the vacuum conduit communicates with the dispensing conduit and is isolated from the suction conduit.

BRIEF DESCRIPTION OF THE DRAWINGS

FIGS. 4A–B are side elevational sectional and top elevational sectional views, respectively, of proximal portions of the fluid dispensing pathway of the medical fluid applicator assembly of FIG. 1, wherein FIG. 4B is taken along line 4B—4B of FIG. 4A.

FIG. 5 is an elevational sectional view of the dispensing assembly of the medical fluid applicator assembly of FIG. 1, taken through the center of the device along line 5—5 of FIG. 2A.

FIG. 6 is a top plan view of a rack used in an actuating assembly and in an audible loudness indicator included in the medical fluid applicator assembly of FIG. 1.

FIG. 7 is a top plan view of the plungers used with the rack in the actuating assembly of the medical fluid applicator assembly of FIG. 1.

FIGS. 9A–E are top elevational, bottom elevational, side elevational sectional, user end elevational, and working end elevational views, perspectively, of the valve stem used in a valve manifold of the suction assembly shown in FIG. 8, wherein FIG. 9C is taken along line 9C—9C of FIG. 9A.

FIGS. 10A–D are top elevational, bottom elevational, and two side elevational sectional views, respectively, of the valve actuator used to actuate the valving of the suction assembly of FIG. 8, wherein FIG. 10C is taken along line 10C—10C and FIG. 10D is taken along line 10D—10D of FIG. 10A.

FIGS. 11A–D are top plan, side elevational, side elevational sectional, and end elevational sectional views, respectively, of a shuttle valve which coordinates the dispensing and clearing mechanisms of the dispensing conduit of the present invention, wherein FIG. 11C is taken along line 11C—11C of FIG. 11A, and FIG. 11D is taken along line 11D—11D of FIG. 11B.

FIG. 17B is a sectional elevational view taken along line 17B—17B of FIG. 17A.

FIG. 17C is an exploded sectional elevational view of one supply device coupling region shown in FIG. 17B.

FIG. 17D is a similar sectional elevational view to FIG. 17B, except taken along line 17D—17D of FIG. 17A.

FIGS. 19A–D are top perspective, side perspective, end perspective, and sectional perspective views of a medical fluid applicator of the present invention with a further variation in the conduit lumen arrangement at the applicator tip portion, wherein FIG. 19D is taken along line 19D—19D of FIG. 19A.

DETAILED DESCRIPTION OF THE INVENTION

Figure 1:
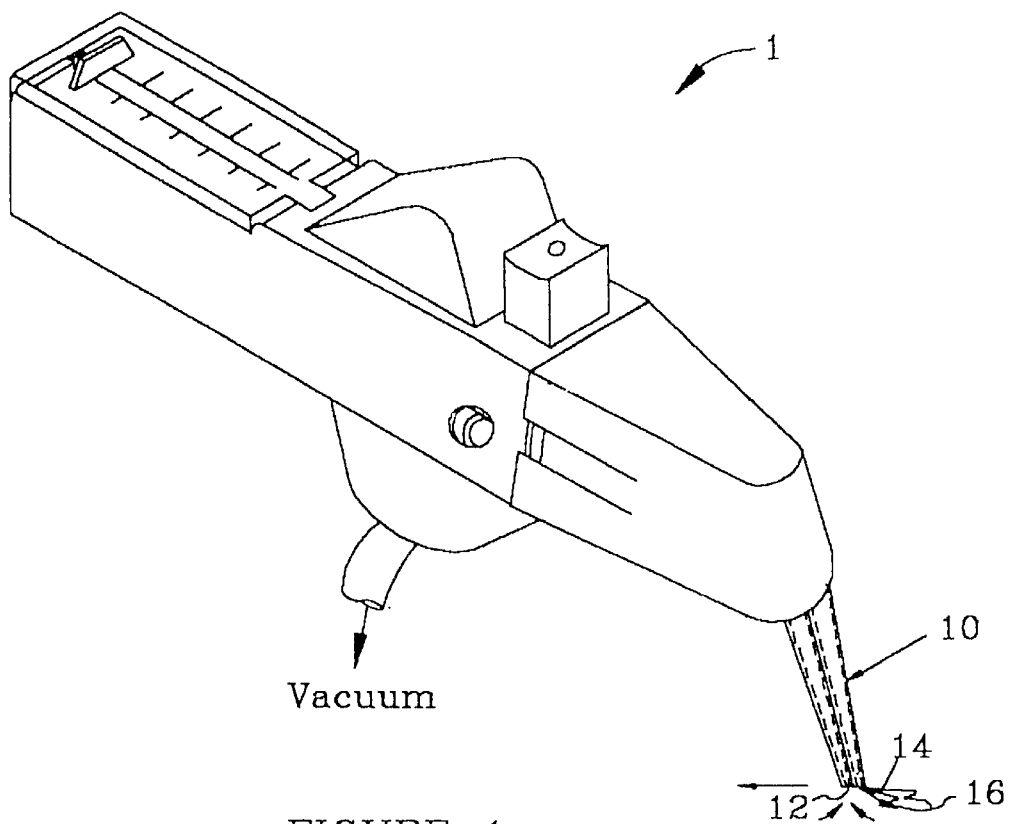
FIG. 1 is an overview perspective view showing the overall medical fluid applicator assembly of the present invention in operation.

The present invention will be illustrated by means of a preferred embodiment shown in the drawings, from which it is to be understood that the medical fluid applicator assembly of the present invention includes a combination of features. One beneficial feature of the current invention is a dispensing assembly which includes a fluid dispensing pathway and an actuating assembly which is closely integrated with an audible loudness indicator that audibly signals the cumulative volume of tissue dispensed. Another beneficial feature of the present invention is a suction assembly which includes a means for shuttling applied vacuum from a suction pathway, which includes a suction conduit at the applicator tip, to a clearing pathway, which couples to the dispensing conduit at the applicator tip. Further to the suction assembly, a further beneficial feature is provided in a valve manifold which allows for selectively controlling the level of applied vacuum at the suction conduit in the applicator tip. Still a further beneficial feature is provided in a filling dispenser assembly which has a keyed coupling with a supply device such that multiple fluid reservoirs in the supply device may be filled with isolated fluids from the filling dispenser in a predetermined arrangement.

Figure 2A:
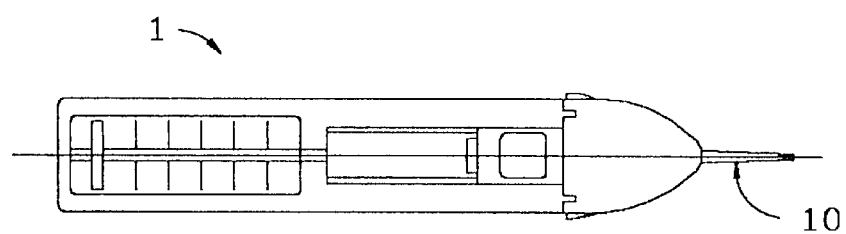
FIGS. 2A–C are top plan, side elevational, and end elevational views of the medical fluid applicator assembly of FIG. 1.
Figures 2B, 2C:
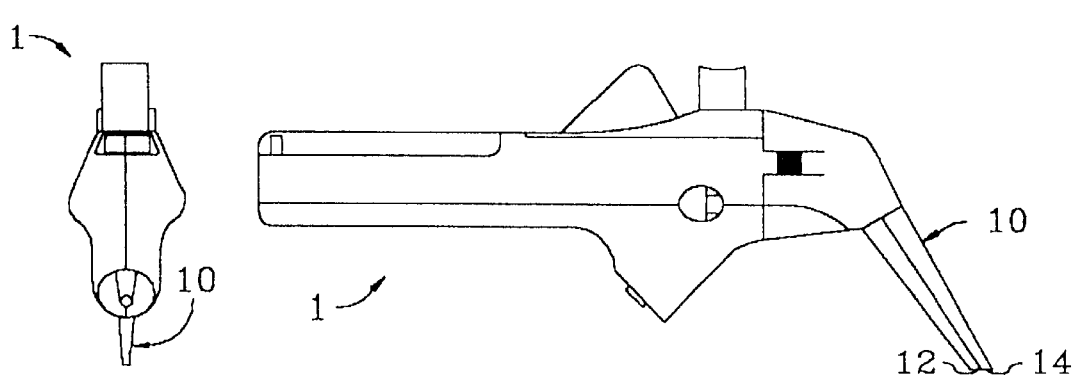
Figure 3:
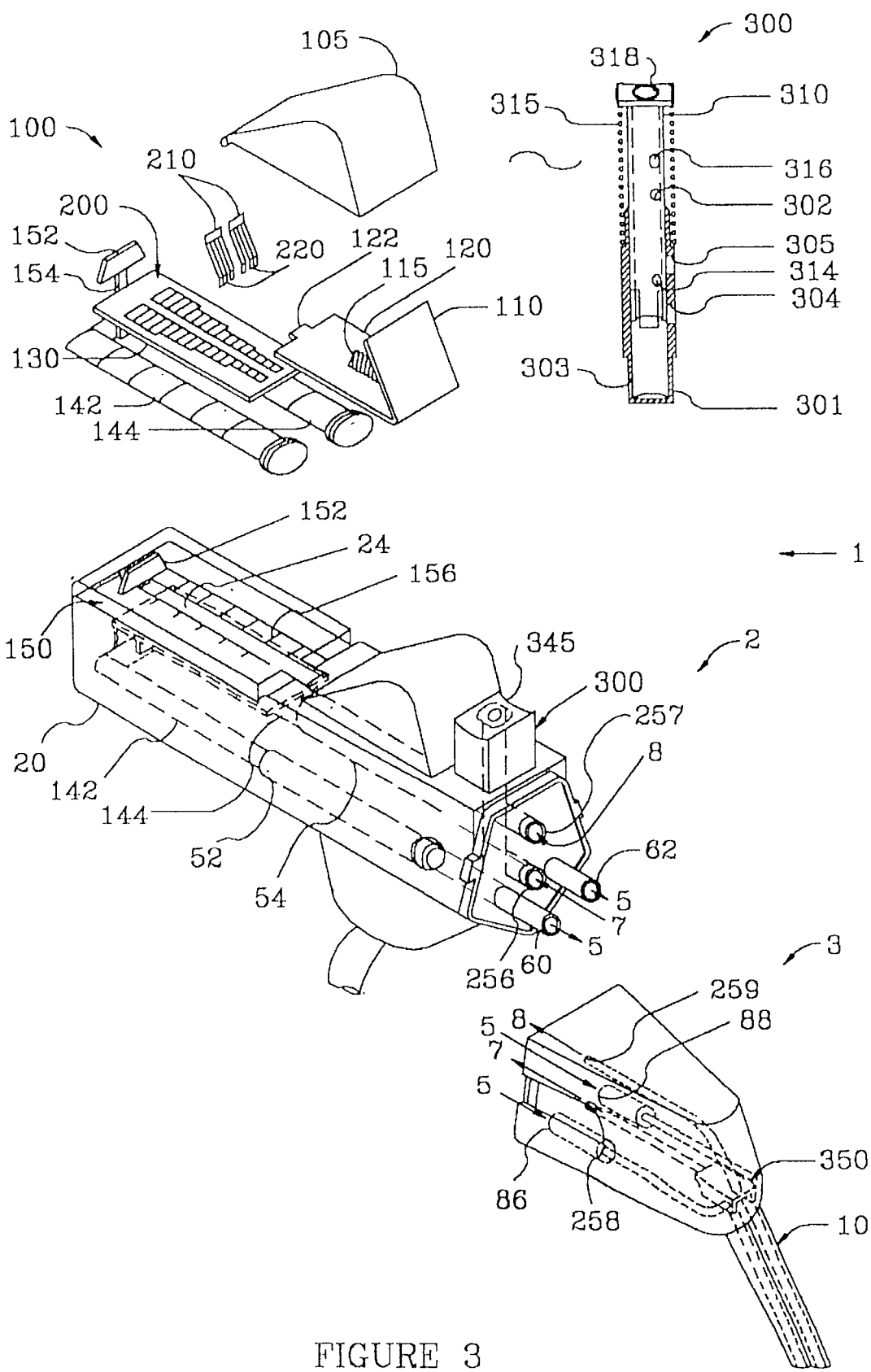
FIG. 3 is an exploded perspective view of the medical fluid applicator assembly of FIG. 1, showing an applicator portion removed from a supply device portion, and further showing the internal structure of the respective portions in shadow, as well as exploded schematic views of portions of an actuating assembly, an audible loudness indicator, and a valve manifold.

Detailed description of these and other beneficial features of the present invention is provided below in reference to the various figures as follows. FIGS. 1–2C provide various perspective views of the overall medical fluid applicator assembly of the present invention. FIG. 3 provides an overview of the removably engageable supply device and applicator portions of the overall device, as well as the overall interior workings of the dispenser and the suction assemblies of the device. FIGS. 4–7 provide increasing detail regarding the dispenser assembly aspects of the present invention. FIGS. 8–14 provide increasing detail regarding the suction assembly aspects of the present invention, including step-wise views of the various suctioning and clearing modes of operating the suction assembly. FIGS. 15–17E provide increasing detail regarding the filling dispenser aspects of the present invention. FIGS. 18A–20C provide various views of alternative applicator tips which are believed to be useful in performing particular types of medical procedures with the present invention.

Referring to a general overview of the device by reference to FIGS. 1–2C, medical fluid applicator assembly (1) is shown in overview fashion in FIG. 1 during one mode of operation as a tissue adhesive or sealant applicator. Applicator tip (10) of the device is shown with an arrow as it is withdrawn across a tissue surface (not shown) such that the tip suction aperture (12), which is coupled to a vacuum source, leads the tip dispensing aperture (14), which is coupled to a tissue adhesive source, across the tissue surface. In this manner, vacuum applied to the tip suction aperture (12) aspirates fluids from the tissue to thereby prepare the tissue for fluid application. As the tip dispensing aperture (14) translates across the tissue surface immediately behind tip suction aperture (12), a trail of tissue adhesive (16) is dispensed onto the prepared tissue.

It is believed that a close proximity in time between tissue preparation and fluid application has a particularly useful application in dispensing tissue adhesives onto tissue surfaces in wound closure procedures. As would be apparent to one of ordinary skill, the remaining detailed disclosure below describes additional novel operating features of the present invention, in addition to the features shown in FIG. 1 which provide for tissue preparation contemporaneous with fluid application.

As shown in FIG. 3, the inner workings of medical fluid applicator assembly (1) are divided between supply device portion (2) and applicator portion (3) which is removably engageable to supply device portion (2). As is apparent to one of ordinary skill by reference to FIG. 3, when applicator portion (3) and supply device portion (2) are engaged, proximal and distal portions of a fluid dispensing pathway (5), a suction pathway (7) and a clearing pathway (8) are coupled, respectively. These pathways thereafter allow for fluid dispensing, applied suction, and clearing of the applicator tip, respectively, as will be apparent to one of ordinary skill from the more detailed description provided below.

Figure 4A:
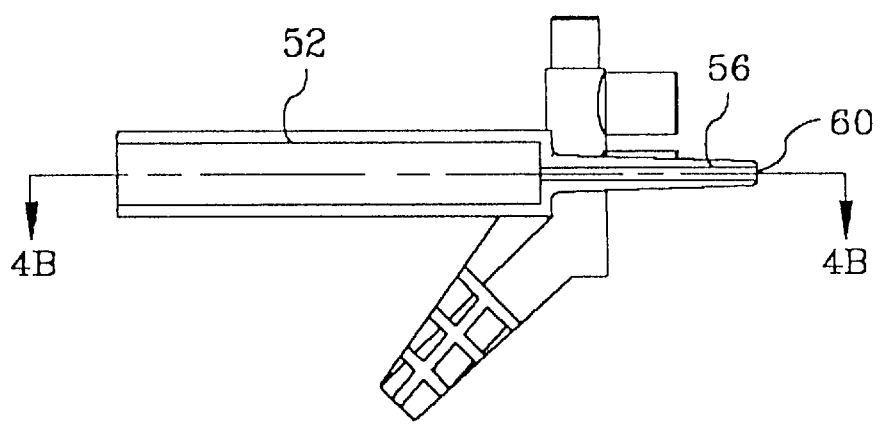
Figure 4B:
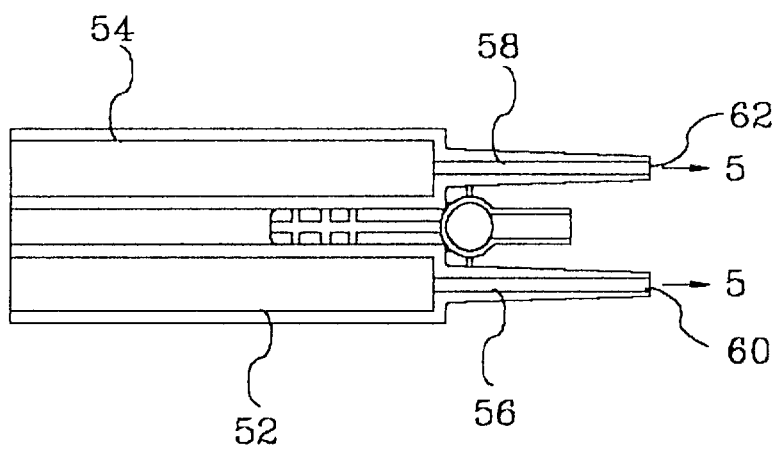
Figure 4C:
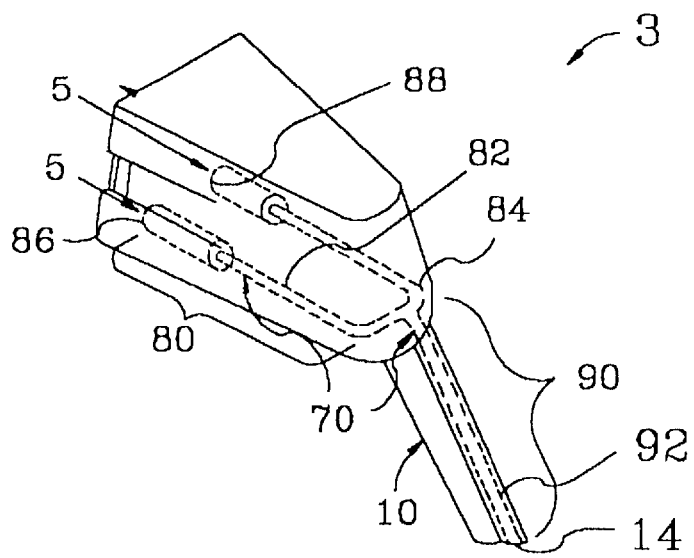
FIG. 4C is a perspective view of the applicator portion of the assembly of claim 1, further showing a dispensing conduit in shadowed view as the distal end portion of a fluid dispensing pathway.

The various components of the dispenser assembly of the current invention are generally shown in FIGS. 3–7 to include an overall dispensing pathway (5), the proximal portions of which being shown in detail in FIGS. 4A–C, and also an actuating assembly (100) for dispensing fluid through that pathway, shown in detail in FIGS. 5–7.

Regarding the components of the fluid dispensing pathway (5) as shown variously throughout FIGS. 3–4C, proximal portions of that pathway within the supply device portion are shown in FIGS. 4A–B to include two reservoirs (52,54) which communicate with two supply conduits (56, 58), respectively. Supply conduits (56,58) extend distally therefrom and terminate distally in two supply ports (60,62), respectively.

It is to be further appreciated by one of ordinary skill that the reservoirs of the fluid dispensing pathway can take a number of forms as long as they are adapted to contain the desired fluid, are pressurizable by an engaged actuating mechanism, and are coupled to a dispensing conduit for distal flow. In the embodiment shown throughout the figures, the reservoirs are tubular chambers which are pressurizable as syringes by means of slideably engaged plungers. In an alternative embodiment not shown, the reservoir may instead comprise a flexible bulb or tube that may be directly compressed, which compression may also be accomplished by means of a plunger. Any suitable arrangement whereby the application of pressure to the reservoir attached to the dispensing means will result in application of the contained fluid is acceptable.

Distal portions of fluid dispensing pathway (5) located within applicator portion (3) are shown in shadow in FIG. 4C. Here, dispensing conduit (70) has a branched portion (80) and a mixed portion (90) that resides in part within applicator tip (10). Branched portion (80) includes two branched conduits (82,84) which terminate proximally in proximal dispensing ports (86,88), respectively. The branched conduits (82,84) merge at the proximal end of mixed conduit (92), which extends distally therefrom through applicator tip (10) where it terminates at tip dispensing aperture (14).

Therefore, it should be apparent to one of ordinary skill by reference to FIGS. 3–4C that fluidly coupling supply ports (60,62) and dispensing ports (86,88) at the supply device/ applicator portion interface creates interface fluid dispensing pathway (5) which includes reservoirs (52,54), supply conduits (56,58), branched conduits (82,84), and mixed conduit (92).

Actuating assembly (100) is also shown in overview fashion in FIG. 3, with more detailed reference to the components thereof provided with reference to FIGS. 5–7.

In overview, actuating assembly (100) includes trigger (105) which is mechanically coupled to two parallel plungers (142,144), which are in-turn coupled to the fluid dispensing pathway via slideably engagement within reservoirs (52,54), respectively. By manually depressing trigger (105), plungers (142,144) advance within reservoirs (52,54) to thereby pressurize the fluids and dispense them distally therefrom and through the remaining portions of the fluid dispensing pathway.

Referring to the detail of actuating assembly (100) shown in FIGS. 5-7, trigger (105) is coupled to pawl (120) via lever arm (110). Spring (115) is further shown with one end engaged with lever arm (110) and the other end engaged with pawl (120). In this arrangement, both trigger (105) and pawl (120) have a spring bias such that trigger (105) has a first resting position and pawl (120) has a reward resting position. Pawl (120) is further shown in FIG. 5 to include a hook (122) which has a flat distal face (124) and a radiused proximal face (126). Hook (122) functions to engage pawl (120) with rack (130).

Rack (130) is further shown in FIGS. 5–6 to include a rack face having a plurality of teeth (132) which border either side of a longitudinal groove (133) extending along that rack face. These teeth (132) are longitudinally spaced with a gap (134) which is adapted to receive hook (122), each tooth including a radiused distal face (136) and a flat proximal face (138). At the proximal end of rack (130), engaging arm (139) is shown as a branched arm extending downwardly to engage at least one of plungers (142,144).

The actuating assembly shown and described further includes a decoupling mechanism, which is shown in-part in FIGS. 5 and 6 (not included in the view of the dispensing assembly shown in FIG. 3). A narrow decoupling arm is shown in FIG. 5 as a longitudinal extension of tab (152) and includes a plurality of sloped cain surfaces (131) which resides within rack (130) and which rest on a bottom face of the rack in confronting engagement with a plurality of sloped decoupling surfaces, such as sloped decoupling surface (135). The decoupling arm may be adjusted upwardly through the upper face of the rack through longitudinal groove (133) by moving the decoupling arm proximally within the rack to allow the arm to be lifted by the sloped decoupling surfaces. The decoupling arm is further limited in its longitudinal motion within the rack such that the tab engaged to the arm may be used to withdraw the rack, and therefore the plungers engaged therewith, proximally within the outer casing of the device housing.

Each of plungers (142,144) of actuating assembly (100) (FIG. 5) includes a proximal shaft and a distal head, as is shown by example at proximal shaft (146) and distal head (148) in FIG. 7. Plungers (142,144) include a plurality of splines (147) which are spaced in order to receive and mechanically engage engaging arm (139) therebetween. Distal head (148) is configured of geometry and material to slideably but frictionally engage the interior wall of one of the fluid reservoirs. As such, distal head (148) is adapted to slide within the corresponding reservoir during forward advancement of the plunger in order to pressurize the fluid within that reservoir. Yet, distal head (148) is also adapted to be frictionally in contact with the reservoir's inner bore in order to prevent backflow of the pressurized fluid. In one variation, an elastomeric member such as an O-ring may be included, such as O-ring (149) shown in FIGS. 5 and 7.

Closely integrated with the operation of actuating assembly (100) are visual volume indicator (150) and audible loudness indicator (200), as shown in overview fashion in FIG. 3.

Visual volume indicator (150) is shown in FIG. 3 and also in FIG. 5 to include a tab (152) which rests above the housing of the device which is shown as outer casing (20). Tab (152) is coupled to lower arm (154) that extends downwardly through longitudinal groove (24) (FIG. 3) in the upper surface of outer casing (20) and is further engaged to rack (130). Visual graduations (156) are provided on the upper surface of outer casing (20), which graduations correspond the relative position of tab (152) to known volumes of fluid delivery.

The mechanism of an audible loudness indicator (200) is herein described also by reference to FIG. 3, as well as to FIGS. 5 and 6. Audible loudness indicator (200) includes a striker (210) which is actuated by teeth (132) to emit audible tones of varying pitch or loudness as fluid is cumulatively dispensed over a range of discrete, incremental volumes of fluid. Striker (210) is secured to the interior of outer casing (20) with fixed positioning relative to the longitudinal motion of rack (130) and includes a plurality of striker arms (220) (FIG. 3) which are spaced laterally across the face of rack (130).

Teeth (132) are further shown to include various regions along the longitudinal axis of rack (130), such as regions (137,139) shown in FIG. 6. Each region has a unique lateral position on the rack relative to the adjacent regions and is thereby adapted to strike a unique combination of laterally spaced striker arms (220) when advanced distally across striker (210), as would be apparent to one of ordinary skill. The distance between the leading edges of each region generally corresponds to an incremental distance of longitudinal travel for rack (130) relative to striker (210) with fixed relative positioning. This incremental distance of travel for rack (130) further corresponds to a predetermined, incremental volume of actuated fluid delivery. Therefore, this arrangement allows for a unique tone to be emitted from a unique combination of striker arms (220) at each discrete, incremental volume of fluid delivered. Therefore the cumulative volume of fluid delivered is recognized by the unique loudness or pitch of emitted tone since the extent of forward positioning of rack (130) within outer casing (20) corresponds with a specific regions of teeth (132) that strike unique combinations of striker arms (220).

It is to be further understood by one of ordinary skill that the particular mechanism disclosed for varying the pitch or loudness of audible signals should not limit the breadth of scope for the present invention. For example, in the embodiment shown, striker arms (220) are shown to be relatively uniform in size and geometry and the various regions of teeth (132) are shown to simply vary in length while sharing common central regions which may engage some of striker arms (220). In this arrangement, it is the number of actuated striker arms (220) which varies with the tooth regions, which corresponds to a change in loudness or volume of tone emitted for each region. However, other arrangements may also be suitable. In one alternative embodiment not shown, the geometry or material of the striker arms may vary along the striker, wherein each unique arm may emit a uniquely pitched tone. In combination, the teeth regions may be as shown in the figures with common striking portions, or may be shifted to only actuate audible signals from entirely unique sets of teeth, as would be apparent to one of ordinary skill.

Moreover, other mechanisms than the rack teeth mechanism shown and described may be suitable for varying the tone or pitch of an audible signal as fluid delivery is actuated. For example, the teeth may be fixed within the casing of the device, with the striker translating across those teeth as an actuator delivers fluids. Alternatively, the teeth might be positioned along a helical path of a screw, the striker being adapted to engage that path and thereby actuated for tone emission by the teeth there.

Still further, other mechanisms than the shown teeth/ striker mechanism may be acceptable, such as an optical or electronic reader which observes changing indicia of actuated fluid delivery and which is thereby coupled to an electronically or electrooptically actuated audible signaling means, as may be apparent to one of ordinary skill. In any case, any variation which audibly emits signals as indicia of cumulative volume of fluid delivery should be considered as a part of the current invention.

The operation of dispenser assembly of the current invention is also shown in two modes in FIG. 5, wherein actuating assembly (100) is shown actuated through one full range of motion or "stroke" of actuating trigger (105). As is evident to one of ordinary skill by reference to FIG. 5, depressing trigger (105) through one stroke actuates forward movement of pawl (120) from a reward resting position to a forward actuated position (shown in dashed line). This motion is achieved by flat distal face (124) of hook (122) confronting the flat proximal face (138) of teeth (132) such that the forward movement of pawl (120) pulls rack (130) forward. As rack (130) pulls forward, plungers (142,144) engaged to rack (130) are also actuated to move forward into the bore of the fluid reservoirs, as is shown at fluid reservoir (52). As the fluid in the reservoirs are pressurized with the forward motion of plungers (142,144), that fluid is dispensed distally through the fluid dispensing pathway, originating from the reservoirs and flowing from the supply device portion and into the applicator portion through the supply ports.

The dispenser assembly shown and described for the current invention is filled (or refilled after completion of fluid dispensing) as follows. Filling is initiated with the rack and the plungers in a fully forward and actuated position. The tab engaged to the rack and to the narrow decoupling arm also has a forward position. The device is coupled to a filling dispenser, such as the novel filling dispenser shown and described with reference to FIGS. 15–17E below. The tab is then manually withdrawn through the longitudinal groove in the outer casing of the supply device. By doing so, the cam surfaces on the bottom face of the disengaging arm slide across the decoupling cam surfaces on the bottom face of the rack until reaching the stop within the rack, thereby lifting the disengaging arm upwardly through the longitudinal groove in the upper face of the rack to lift the hook of the pawl and disengaging it from the teeth on the rack surface. Continued proximal movement of the tab relative to the outer casing of the device also pulls the plungers and the rack rearwardly to create a vacuum to fill the reservoirs and to also reposition the rack proximally so the hook on the pawl returns to the front part of the rack.

The spring-biased resting position of trigger (105) further corresponds to a rearward or proximal position for pawl (120) relative to the longitudinal axis of outer casing (20).

When the trigger (105) is released, spring (115) restores the trigger and also the pawl to their original position, while the striker remains in its advanced position along the regions of the teeth on the forward actuated rack. Moreover, the spring-bias and mechanical constraints on the motion of lever arm (110) and pawl (120) within outer casing (20) also limit the range of available motion for trigger (105) from the spring-biased resting position to a fully actuated position, thereby defining the full "stroke" range. The combined features of the overall actuating assembly are adapted such that the available "stroke" range of actuated motion corresponds to a predetermined incremental volume of fluid delivery actuated from the fluid reservoir.

Moving to the suction assembly of the current invention, FIG. 3 provides an overview of the overall suction assembly, while FIGS. 5 and 8–12C provide increasingly more detail of the components and mechanisms of operation thereof.

Figure 8:
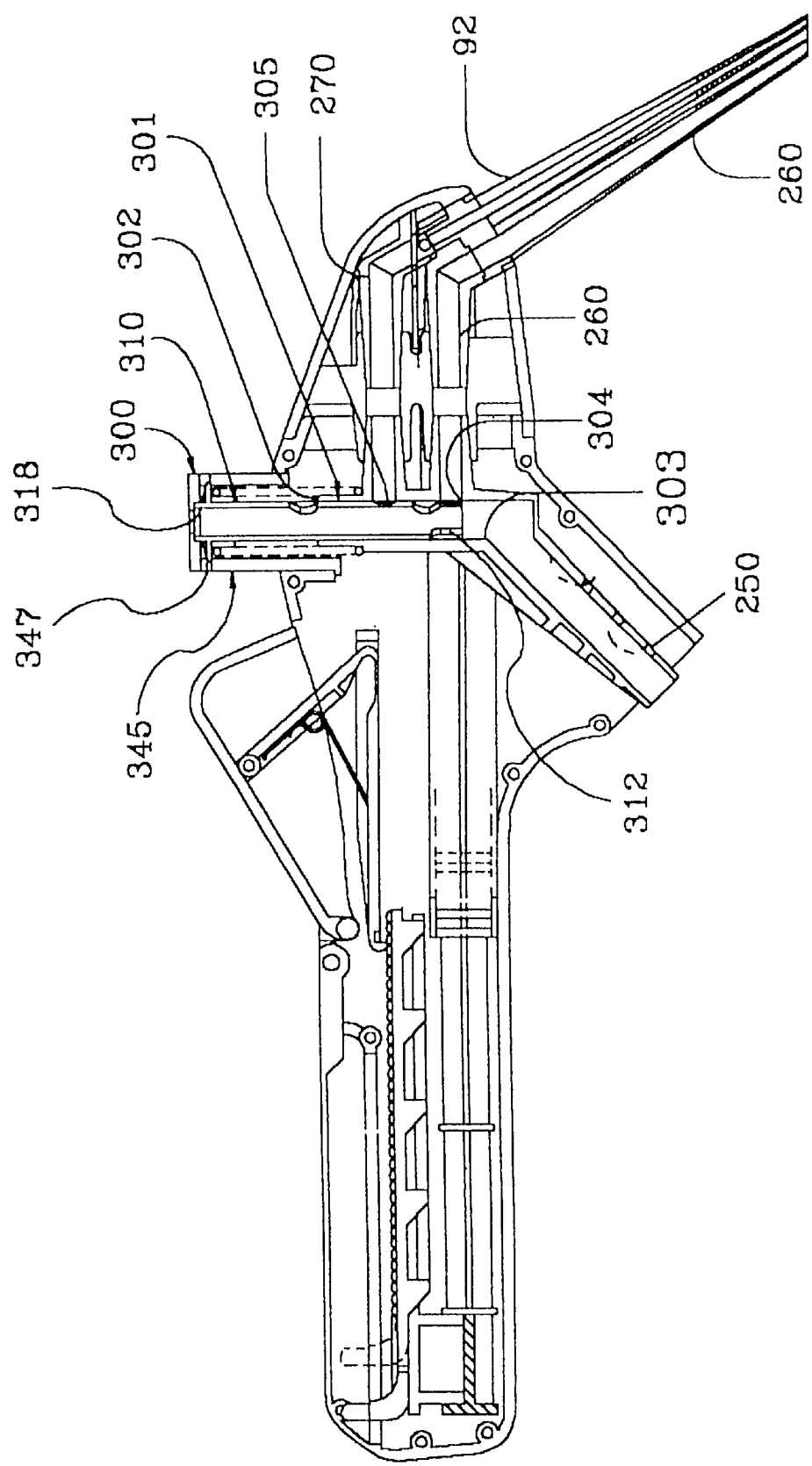
FIG. 8 is a similar elevational sectional view of the medical fluid applicator assembly as shown in FIG. 5, although showing both the supply device portion and the applicator portion in sectional view to show the suction assembly of the current invention.

The proximal portions of the suction assembly located within supply device portion (2) are shown in FIG. 5 to include a vacuum conduit (250) which is selectively coupled to vacuum coupling ports (256,257) by vacuum manifold (300). The distal portions of the suction assembly located within applicator portion are shown in FIG. 8 and include a suction conduit (260), a clearing conduit (270). Comparing the overall device assembly shown in FIG. 8 with the removed view of supply device portion (2) and applicator portion (3) in FIG. 3, it should be apparent to one of ordinary skill that clearing conduit (270) is formed by coupling and aligning supply device suction port (256) with applicator suction port (258), and similarly coupling and aligning supply device clearing port (257) with applicator suction port (259) (FIG. 3) to form one contiguous channel between the valve housing and the mixed portion of the dispensing conduit.

FIGS. 11A–D and 14A–B further show a shuttle valve (350) which is further included in the distal portion of the suction assembly for adjusting applied vacuum between the suction conduit (260) and the clearing conduit (270). As will be disclosed in further detail below, the valve manifold (300) operates to adjust the proportions of applied vacuum from the vacuum conduit (250) to either the suction conduit (260), when suction at for tissue preparation prior to dispensing, or to the clearing conduit (270), when suction is desirably used to clear coagulated tissue adhesive proximally from the mixed portion (90) of dispensing conduit (70).

The operable features of valve manifold (300) are shown in FIG. 8, and include valve housing (301) which houses valve stem (310) in moveable engagement.

Valve housing (301) is shown in FIG. 8 to form an elongate bore having an open top in communication with atmospheric pressure and which functions as a vent port (302). Furthermore, the wall forming the inner bore of valve housing (301) further includes a suction port (304) and a clearing port (305) on the distal side of valve housing (301). Vacuum port (303) communicates with vacuum conduit (250), while suction port (304) and clearing port (305) communicate with vacuum coupling ports (256,257), respectively.

Valve stem (310) is shown variously in FIGS. 3, 5, and 8, and in more detail in FIGS. 9A–D, and generally includes a valve chamber (311), a vacuum aperture (312), a suction aperture (314), a clearing aperture (316), and a vent aperture (318), which apertures are shown in detail in FIGS. 9A–D. Valve stem (310) is generally an elongate tubular member which has an outer diameter adapted to frictionally engage the inner surface of valve housing (301)(FIG. 8). Valve stem (310) is also slideable within valve housing (301), however, and is thereby adjustable between various positions along a predetermined range of motion. According to the embodiment shown throughout the figures, valve stem (310) has a vertical range of motion within valve housing (301) in order to adjust the relative positioning of the various valve apertures for selective registry with the various ports in the valve housing, as will again become more apparent with reference to FIGS. 12A–14B below. This range of motion is in part limited by the spring which also gives the valve stem a spring-bias in the upward resting position where there is no applied suction.

More detailed description of the various valve apertures and ports as shown in FIGS. 8 and 9A–E is as follows. Vacuum aperture (312) includes an open bottom of valve stem (310) and also an elongate open slot on the proximal side of valve stem (310). Suction port (314) and a clearing port (316) which are positioned at particular respective positions along a common vertical plane of valve stem (310). In addition, valve stem (310) further includes an open vent aperture (318) which selectively communicates exteriorly of valve chamber by manually covering or uncovering that opening.

Further to the design of valve stem (310) and its apertures as shown in FIGS. 9A–D, each of suction aperture (314) and clearing aperture (316) is shown to be a non-circular shaped opening having an elongate axis aligned with the longitudinal axis of valve stem (310) (shown in dashed line in FIG. 9E), a wide axis, and a short axis, such as are shown at long axis "L", wide axis "W", and short axis "S" for clearing aperture (316). Wide axis "W" has a larger cross-sectional area than the cross-sectional area of short axis "S" in the perpendicular plane to long axis "L". For the purpose of further understanding, this described shape may be considered a "tear-drop" shape, or a "diminished elliptical" shape. In addition, the wide and short axes of clearing aperture (316) are provided in an inverse reciprocal orientation along the longitudinal axis relative to the respective orientation of suction aperture (314). The primary purpose for this inverse reciprocal orientation of long and short axis for suction aperture (314) and clearing aperture (316) is in one particular mode of operation wherein clearing aperture (316) is used as a vent in a venturi valve-role for controlling the level of suction applied to suction conduit (270), as will be developed further below with reference to FIGS. 13A–B. Nevertheless, it should be apparent to one of ordinary skill that the short axis leads the wide axis for suction aperture (314) during a downward vertical motion of valve stem (310) along its longitudinal axis, while the wide axis instead leads the short axis for clearing aperture (316) during that range of motion.

A valve actuator (345) is further shown in FIGS. 3, 5, and 8, and in further detail in FIG. 10A–D. Valve actuator (345) can be considered to be a part of the overall assembly for valve manifold (300), as well as for shuttle valve (350), as will be developed below. Valve actuator (345) is generally a button which has a button bore (346) that is adapted to fit over valve stem (310) such that actuator vent aperture (347), which is provided at the top surface of valve actuator (345), is adapted to align with vent aperture (318) of valve stem (310) when engaged to the top of the valve stem. Near the bottom region of valve actuator (345) is a cam actuator surface (348) which includes at least one stop, such as that shown at stop (349). Cam actuator surface (348) is adapted to engage a cam surface of a shuttle valve when valve manifold (300) is adjusted toward downward position within valve housing (301) in order to actuate movement of the shuttle valve to initiate a suction clearing operation, which will be developed below with reference to FIGS. 14A–B.

FIGS. 11A–D show shuttle valve (350) which is adapted to be actuated by valve actuator (345) (FIGS. 10A–D) for use in a clearing mode of operating the medical fluid applicator of the current invention. Shuttle valve (350) functions to selectively and alternatively couple the mixing conduit portion of the dispensing conduit either to the branched portion for dispensing fluids or to the clearing conduit for retrogradedly clearing clogged adhesive from the mixing conduit.

Shuttle valve (350) is shown in FIGS. 11A–D to include a body (352) which includes a dispensing valve portion (360), a clearing valve portion (370), and a proximal portion having a cam surface (380). Dispensing valve portion (360) includes two vertical splines (362,363) which are parallel to the longitudinal axis (dashed line) of shuttle valve (350). Vertical splines (362,363) have dispensing conduit apertures (364,365), respectively, which extend therethrough in a transverse horizontal plane relative to the longitudinal axis. Vertical splines (362,363) further have closed regions which are adjacent the corresponding dispensing conduit apertures, such as is shown in FIG. 11B at closed region (366) for vertical spline (362) and in FIG. 11C at closed region (367) for vertical spline (363). Clearing valve portion (370) includes a horizontal face (372) which extends between vertical splines (362,364) and which further includes a clearing conduit aperture (374) therethrough in an angled vertical plane relative to the longitudinal axis. At least one seal member (390) is further shown to be disposed upon the outer surface of the respective valve portions, which seal member is preferably an elastomeric or compressible material, such as an elastomeric polymer or a rubber.

The means for actuating shuttle valve (350) in order to operate the suction shuttling function of the current invention is further shown in FIGS. 11B–C. Cam surface (380) is disposed on an angled vertical plane relative to the longitudinal axis of shuttle valve (350). In this orientation, cam surface (380) is adapted to slideably engage cam actuator surface (348), as is further shown in FIG. 11C. As the valve actuator (345) is depressed in a downward motion, cam actuator surface (348) contacts cam surface (380). Further downward motion of valve actuator (345) forces shuttle valve (350) to advance transversely to the motion of valve actuator (345) and in the longitudinal plane of shuttle valve (345). This is because the shuttle valve is restricted from moving within the applicator tip in all directions except longitudinally. The angled interaction between cam actuator surface (348) and cam surface (380) provides the longitudinal component of normal force therebetween to actuate the longitudinal shuttling motion.

Further included in the shuttle valve mechanism of the present invention is a spring bias on the shuttle valve in a rearward resting position, such as by use of a spring which is engaged to the shuttle valve and also to the interior of the applicator portion of the device housing (not shown). The forward actuated movement of the shuttle valve by operation of the actuator works against that spring bias such that upon releasing the actuator the shuttle valve returns to the rearward position.

Figure 12A:
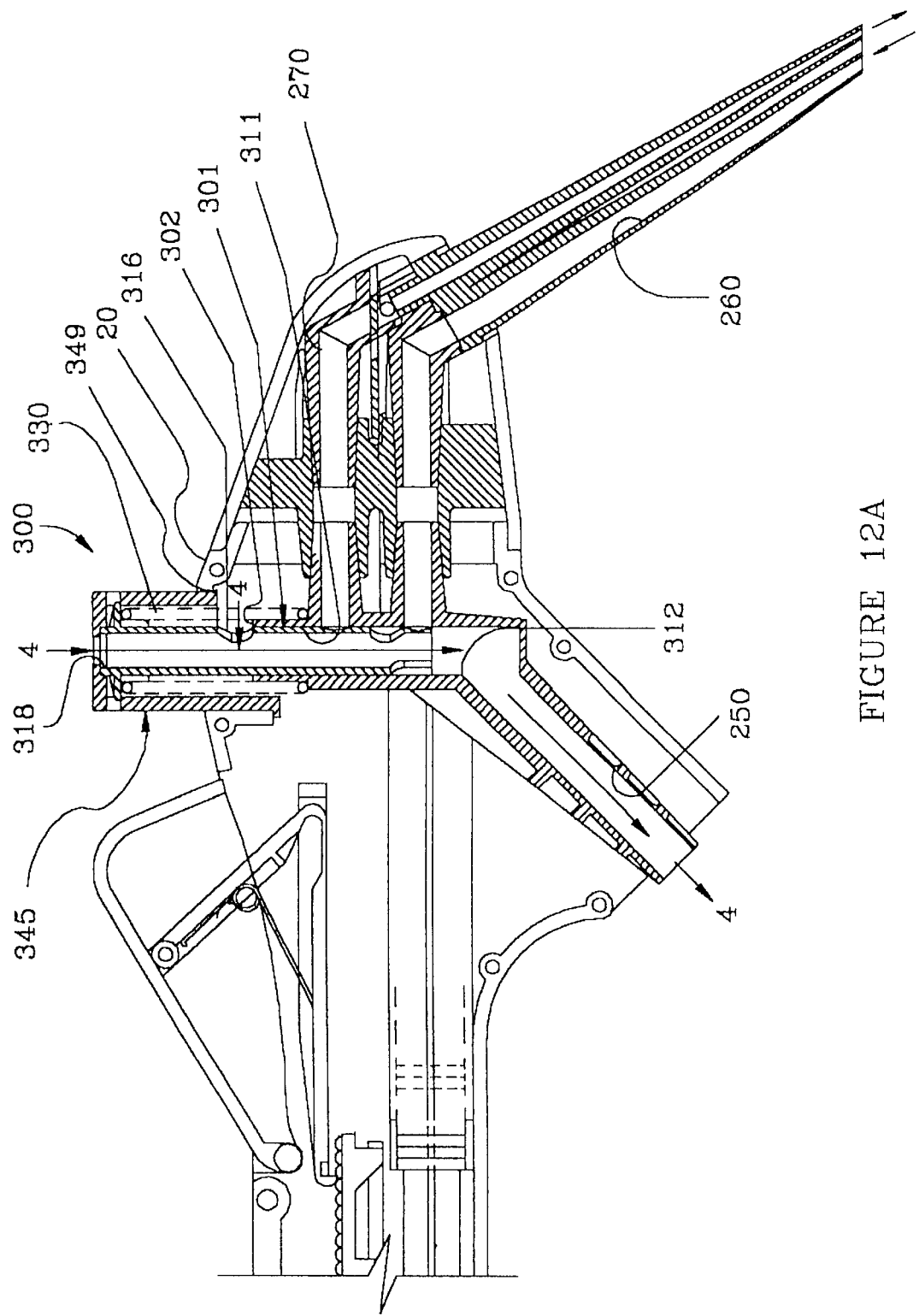
FIGS. 12A–C are exploded side elevational sectional views of the suction assembly of FIG. 8, showing a valve stem in three sequential positions within the valve manifold housing which correspond to an open vent pathway, an open suction pathway, and an open clearing pathway, respectively.
Figure 12B:
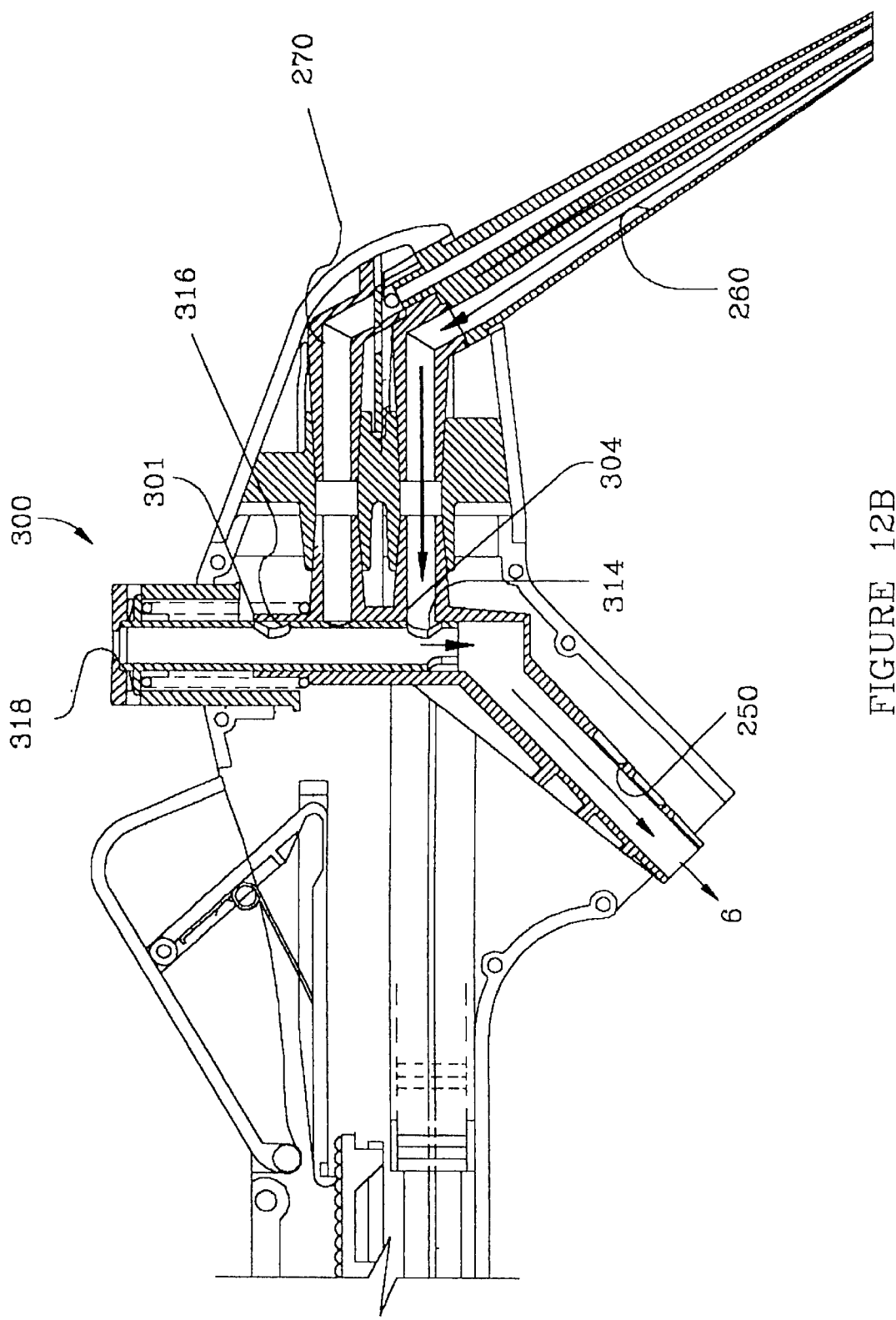
Figure 12C:
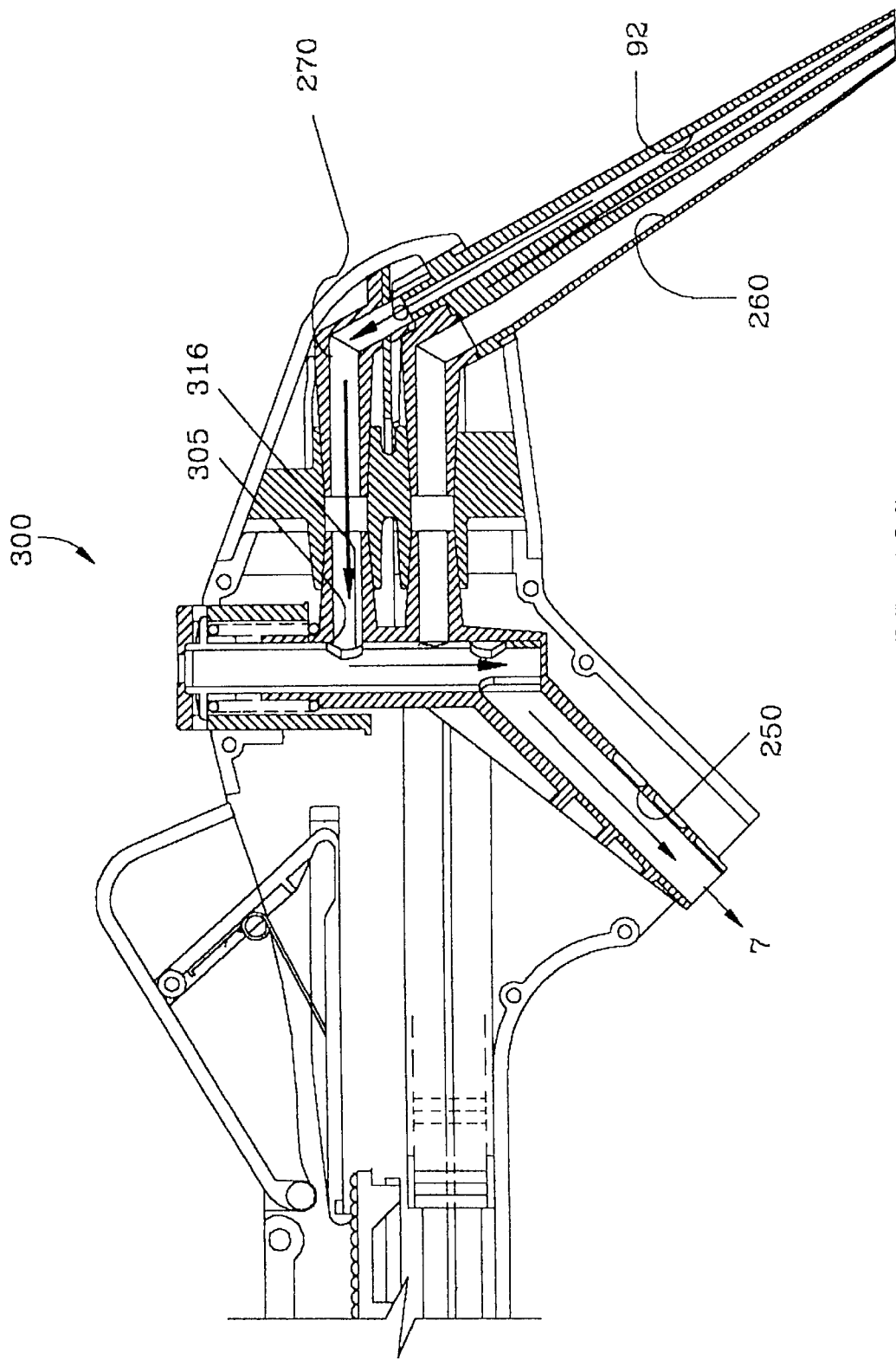
Figure 13A:
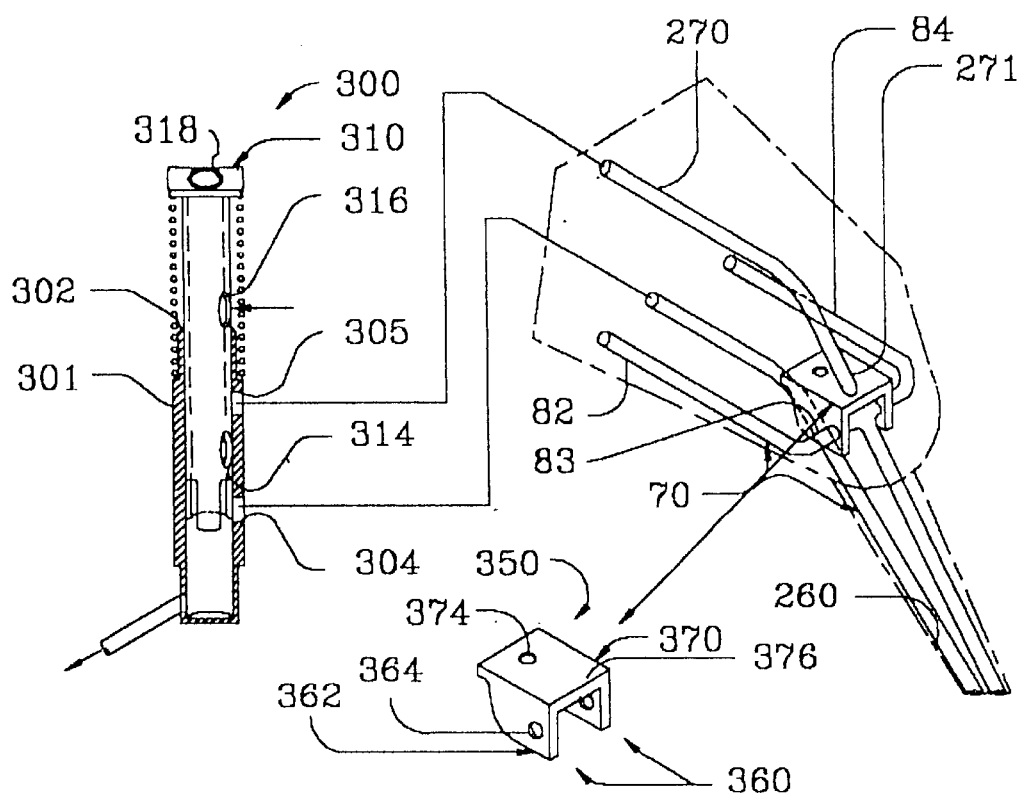
FIGS. 13A–B are schematic representative views of the valve manifold during sequential modes of operation, respectively, in adjusting the amount of applied suction to the suction pathway of FIG. 12B.
Figure 13B:
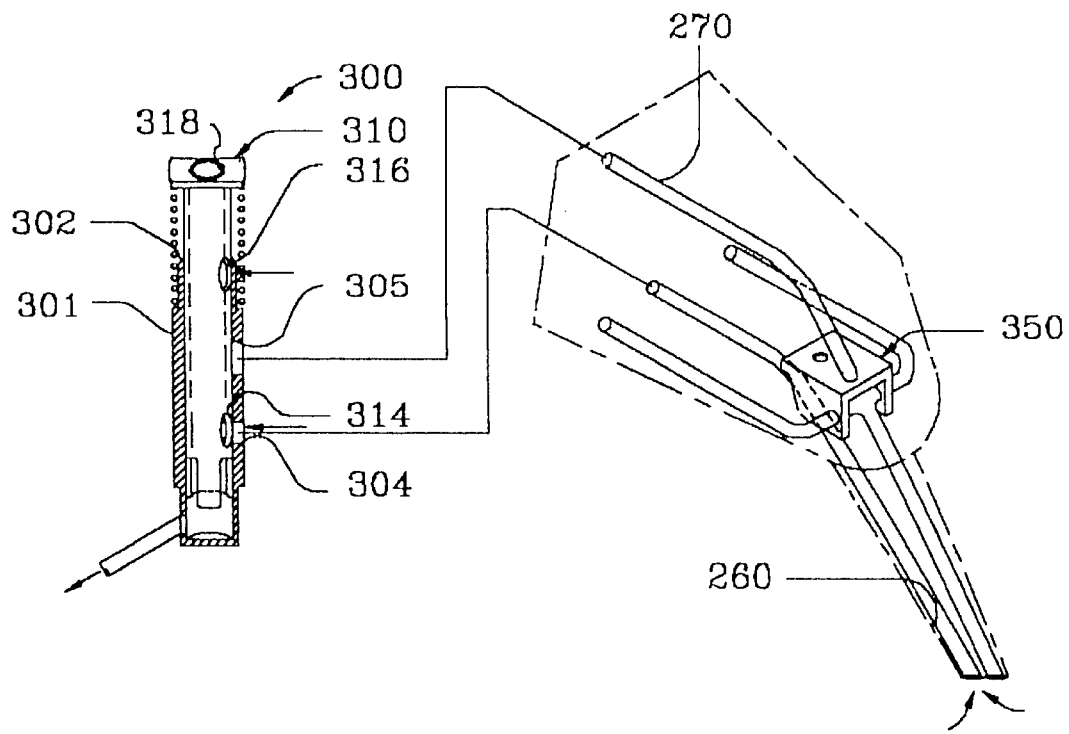
Figure 14A:
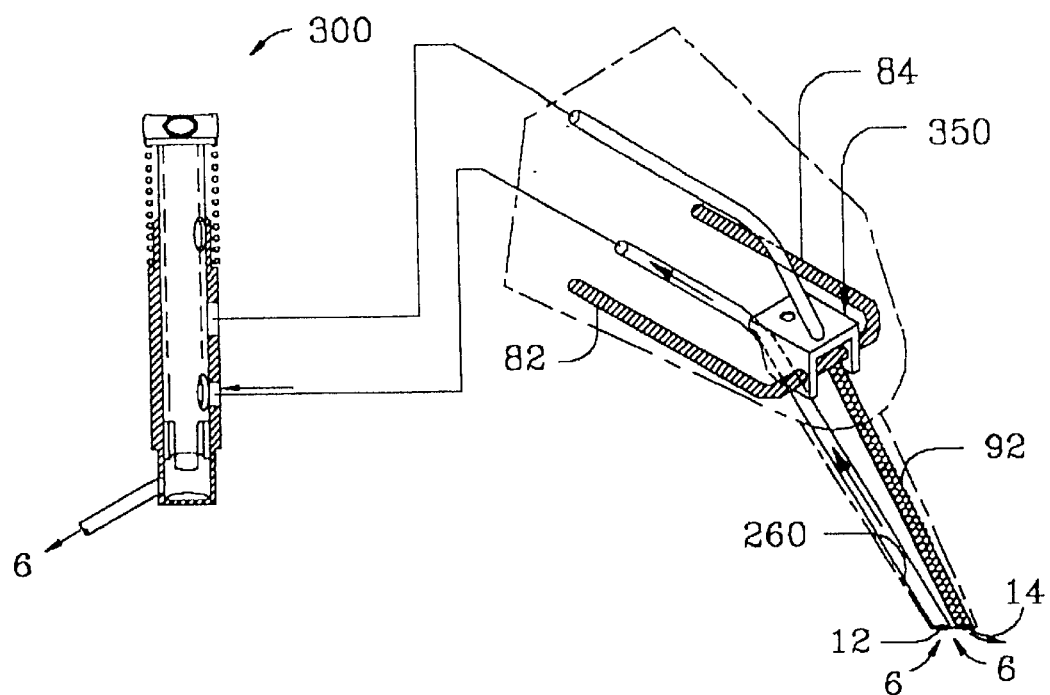
FIGS. 14A–B are schematic representative views of the valve manifold during sequential modes of operation, respectively, in shuttling applied vacuum from the suction pathway of FIG. 12B during fluid application to the clearing pathway of FIG. 12C following fluid application, respectively.
Figure 14B:
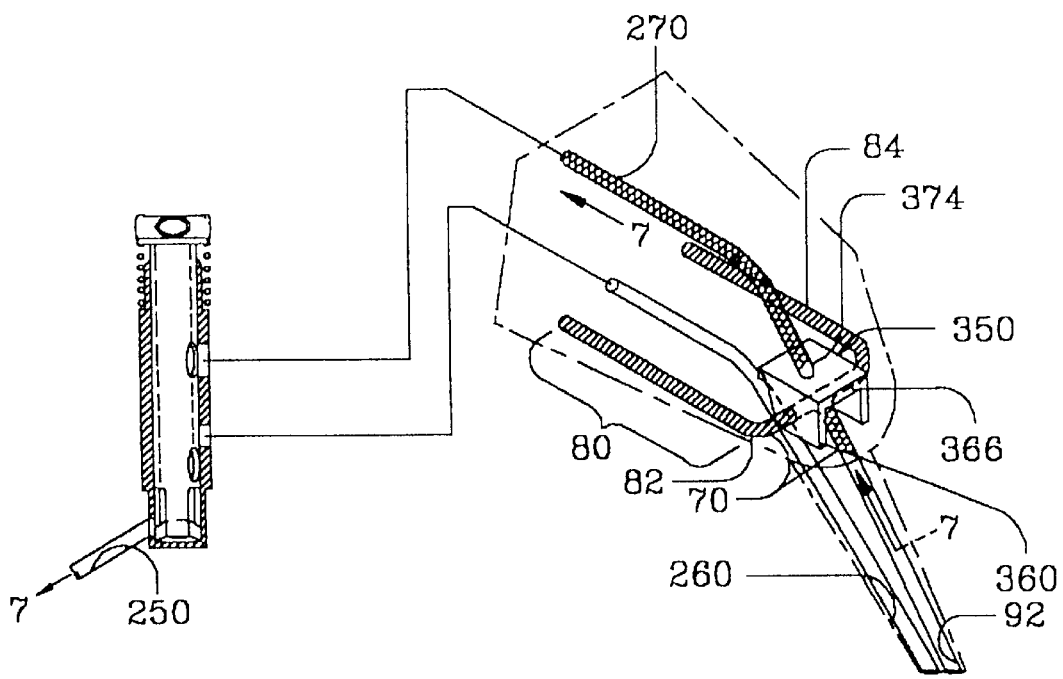

The operation of the suction valving components of the present invention, including the valve manifold and the shuttle manifold, is shown in various modes of operation throughout FIGS. 12A–14B. FIGS. 12A–12C show the relationship of the various positioning of valve manifold (300) in the creation of different pathways for suction through the various available conduits. FIGS. 13A–B schematically shown the positioning of valve manifold (300) and shuttle valve (350) during different modes of venting and suctioning operations at the applicator tip. FIGS. 14A–B show different positions for valve manifold (300) and shuttle valve (350) in the creation of an alternative clearing pathway for applied suction through the clearing conduit to clear the mixed portion of the dispensing conduit.

FIG. 12A shows valve manifold (300) in a venting position such that a vent pathway (4)(bolded arrows) is created and there is no applied suction to suction conduit (260) or clearing conduit (270). In this position, vacuum conduit (250) communicates with valve chamber (311) which is exposed only to atmospheric pressure through vent aperture (318) and the coupling between clearing aperture (316) and vent port (302) above valve housing (301). In this case, clearing aperture (316) functions as another vent aperture. As is apparent in FIG. 12A, this venting position is the resting position for valve manifold due to a spring bias to that position created by spring (330) as stop (349) engage portions of interior surface of outer casing (20).

FIG. 12B shows valve manifold (300) in a first suction position such that a suction pathway (6) is created by registering suction aperture (314) with suction port (304). In this position, vacuum conduit (250) communicates with suction conduit (260) to apply vacuum pressure to that suction conduit in the suction pathway (6). Further, clearing aperture (316) is closed within valve housing (301) and a user's thumb functions to close vent aperture (318) during downward actuation of the valve manifold (300). By maintaining these apertures in a closed condition, the suction pathway (6) is isolated to achieve full vacuum at the applicator tip.

FIG. 12C shows valve manifold (300) is a second clearing position such that a clearing pathway (7) is created by registering clearing aperture (316) with clearing port (305). In this position, vacuum conduit (250) communicates with clearing conduit (270) to apply vacuum pressure to that clearing conduit through clearing pathway (7). The completion of clearing pathway (7), however, is intended to include mixed conduit (92), in order to achieve the intended operation of clearing clogging obstructions from that conduit. This coupling to the dispensing conduit is achieved through the actuation of the shuttle valve, as will be described in more detail with reference to FIGS. 14A–B.

As shown in FIG. 12C, the clearing conduit (270) is coupled to the proximal end of the mixed conduit (92) such that a continuous taper is created with distally reducing inner diameter between those conduits. It is believed that this tapered geometry may enhance the retrograde passing of contents within mixed conduit (92) due to applied suction, particularly when such contents are coagulated or cured tissue adhesive or sealant. Furthermore, it is believed that such taper should preferably be a gradual one. It has been observed that, where too drastic a taper is provided in the clearing pathway, initial proximal movement of the targeted coagulum creates a shunting pathway around the coagulum. This shunting pathway may significantly diminish the proportion of applied vacuum pressure onto the coagulum for withdrawal. However, some taper may be required for a particular fluid matrix to be cleared, due to the frictional dynamics of withdrawing the coagulum through the pathway. Thus, while a gradual taper such as that shown may be sufficient for many fluid delivery applications, other tapered geometries may be more preferable for a particular fluid application, as would be apparent to one of ordinary skill.

The operation of valve manifold (300) in performing applied suction to suction conduit (260) is further shown schematically by reference to FIGS. 13A–B. In particular, the relationship between clearing aperture (for venting purposes) and suction aperture are shown in achieving different selected levels of applied suction at suction conduit (260).

FIG. 13A shows the valve manifold in the resting or venting position, similar to that shown in FIG. 12A. There is no suction at suction port (304), nor at clearing port (305) because neither of the respective suction or clearing apertures (314,316) is aligned therewith, and instead the wall of valve stem (310) blocks communication through those ports. Venting is achieved in this position either through vent aperture (318) or through clearing aperture (316), which communicates with atmospheric pressure above the top of valve housing (301) through vent port (302), or through both (bolded arrows). In one mode during initial actuation of valve manifold (300) to various actuated positions, vent aperture (318) is manually blocked and full venting is achieved through clearing aperture (316).

FIG. 13B shows the valve manifold after actuation to a suctioning position within the valve housing which is somewhere between the resting or venting position (such as in FIGS. 12A or 13A) and the first suction position (such as in FIG. 13B). It is to be understood by one of ordinary skill that, between these two positions, suction aperture (314) and clearing aperture (316) translate across and register at least in part with suction port (304) and vent port (302), respectively. It is to be further understood that, during this downward motion of valve stem (310), suction aperture (314) has an increasing cross-sectional area which registers with suction port (304), going from its short axis to its wide axis. Simultaneously, clearing aperture (316) instead has a decreasing cross-sectional area which communicates with atmospheric venting through vent port (302) as its wide axis leads its short axis downwardly into valve housing (301).

Further to the suction valving mechanism as shown in operation in FIGS. 13A–B, a combination of "venturf"-type and "trumpet"-type valve mechanisms are used to achieve controlled suction at suction conduit (260). The term "venturi"-type valve is herein intended to mean a valve mechanism that adjusts applied suction at a working pathway where applied suction is intended by adjusting the degree of parallel venting through at least one vent pathway. The term "trumpet"-type valve is herein intended to mean a valve mechanism which adjusts the applied suction at the working pathway by selectively occluding or opening the cross section of the conduit directly in the working pathway. Clearing aperture (316), when translated across the open vent port (302) and downwardly into valve housing (301), functions as an adjustable venturi-type valve to shunt applied vacuum in a selected manner away from another open suction pathway through suction conduit (260). Suction aperture (314), when translated across suction port (304), functions as a trumpet-type valve to directly adjust the resistance to applied vacuum to suction conduit (260).

In this combination suction valving mechanism of the present invention, it has been beneficially observed that a controllable range of vacuum pressures may be achieved at suction conduit (260), and that a zero vacuum state can also be achieved at that conduit. It is believed that the venturi valve mechanism arises from operating clearing aperture (316) as a vent, and together with the simultaneous adjusting of that vent with the adjusting of a trumpet valve component through the suction aperture operation, provides a controllable range of applied pressures. It is further believed that the inverse orientation of short and wide cross-sectional areas of the venturi (clearing aperture) and trumpet (suction aperture) valving apertures, in relation to the direction of travel during the combination valving function, further enhances the ability to control the applied suction to selected levels. In addition, the trumpet valve component arising from the operation of suction aperture (314) makes the completely closed, zero vacuum condition possible.

It is further contemplated that, while the inversely oriented tear-drop or diminished ellipse shapes for the suction and clearing apertures are considered particularly useful in controlling selected levels of applied suction to a working suction conduit, the invention is not so limited to that particular arrangement of aperture shapes. Various shapes other than the "tear-dropped" shape described and shown for suction and clearing apertures (314,316) may be acceptable in various modes of operating the assembly. For example, circular apertures may be used, or one of the suction or clearing apertures may be circular and the other may be a different shaped, such as the tear-drop shape or diminished ellipse.

More specifically regarding the diminished elliptical shapes of the particular embodiments, the ratio of the elongate axis length to the change in cross-sectional area between short and wide axes along that elongate axis may be adapted for a particular intended use. For example, it is believed that a longer elongate axis, with a more gradual change in cross-sectional area from the short axis to the wide axis of the shape, may provide for a longer length of actuating travel between selected levels of suction, and therefore may result in more sensitive control of minute changes in suction level.

Further to the shuttling operation of adjusting applied suction from selected conduits, FIGS. 13A–B also show the distal portions of shuttle valve (350) as it interacts and couples with the dispensing and suction assemblies. Each of the branched conduits (82,84) and also clearing conduit (270) are shown to include a slotted region, such as slotted region (83) in branched conduit (82) or slotted region (271) in clearing pathway (270), through which the respectively engaged valve portion may be slideably received. Dispensing valve portion (360) and clearing valve portion (370) are engaged within the slotted regions of dispensing conduit (70) and clearing conduit (270), respectively. Actuation of the shuttle valve components through these slotted regions for the purpose of selecting operable fluid pathways in a clearing function is further discussed with reference to FIGS. 14A–B below.

In actuating valve manifold (300) from the vent position to the first suction position (or somewhere therebetween as shown in FIGS. 13A–B), shuttle valve (350) remains in a resting reward position within the applicator portion. This is because, over the range of motion between the two respective valve manifold positions, the cam actuating surface on the valve actuator has not yet contacted the cam surface of shuttle valve (350) to actuate motion thereto (not shown). Further to this rearward resting position shown for shuttle valve (350), actuator dispensing apertures such as actuating dispensing aperture (364) on vertical spline (362) are aligned and registered with the interior lumens of each of branched conduits in their respective slotted regions, which alignment allows for fluid dispensing. However, actuator clearing aperture (374) on clearing valve portion (370) is out of alignment with the interior lumen of clearing conduit (270) in the slotted region thereof, and instead closed portion (376) of valve clearing portion (370) is aligned in that slotted region to block flow therethrough. Further detail as to the mechanism of actuating the valving mechanisms of shuttle valve (350) are further developed with respect to FIGS. 14A–B.

FIGS. 14A–B show schematic views of the role of valve manifold (300) and shuttle valve (350) in the clearing function of the suction assembly of the current invention. FIG. 14A shows the valve manifold positioning and applicator portion during the operation of dispensing a mixed fluid, while FIG. 14B shows a subsequent operation of clearing the mixed fluid from the applicator tip region.

FIG. 14A provides a schematic view of the valving operation of the device during use it tissue preparation prior to dispensing, as shown in perspective view in FIG. 1. Each of two different fluids is shown being dispensed through either branched channel (82) or branched channel (84). Shuttle valve (350) is in the reward resting position to allow the fluids to flow through the dispensing valve portions and mix in mixed conduit (92). The mixture is further shown being dispensed out tip dispensing aperture (14). Simultaneously the fluid delivery just described, valve manifold (300) is shown adjusted to the first suction position (or something close thereto) to allow for suction pathway (6) to couple vacuum pressure to the tip suction aperture (12).

FIG. 14B shows the same schematic view of FIG. 14A after fluid dispensing and during a clearing operation. Shuttle valve (350) is actuated into a forward actuated position. In this position fluid communication is blocked between vacuum conduit (250) and branched conduits (82, 84) via the closed portion (366) of dispensing valve portion (360). Also in this position, communication is opened between vacuum conduit (250) and mixed conduit (92), through clearing conduit (270), via clearing valve aperture (374). The seal members (FIGS. 11A–D) on the dispensing valve and clearing valve portions (360,370) allow for slideable engagement within the respective slotted portions of the engaging conduit lumens, yet substantially maintain fluid integrity at those slotted portions and around the engaging valve portions.

Thus, clearing pathway (7) is created in this shuttling operation, and the mixed fluid in mixed conduit (92) is shown in FIG. 14B as it is withdrawn due to suction through clearing pathway (270). Furthermore, by blocking communication between the branched portion (80) of dispensing conduit (70) and the mixed conduit (92) of dispensing conduit, contents proximal to the shuttle valve within the fluid dispensing pathway, including that in the supply reservoirs (not shown), are isolated from vacuum pressure and also from the contaminating coagulum being withdrawn from mixed conduit (92) (in the case of tissue adhesive applications).

It is further contemplated that the shuttle valve of the present invention may take a different form than that specifically described with reference to FIGS. 11A–D and 13A–14B without departing from the scope of the present invention. For example, rather than the shuttle valve shown and described, the slideable shuttling mechanisms of dispensing valve portion (360) and clearing valve portion (370) through slots in the engaging conduit lumens may be replaced with other types of individual valve mechanisms which may operate separately or in coordination. One example of a suitable alternative may be individual trumpet valve-type mechanisms engaged with each respective conduit lumen to selectively restrict flow therethrough. Any suitable mechanism which is apparent to one of ordinary skill from this disclosure and which allows for the desired selection of open and closed lumens in the dispensing and clearing conduits during the dispensing and clearing operations described is considered within the scope of the current invention. Therefore, where "shuttle valve" is used throughout this disclosure, it should be apparent that these other suitable valving alternatives are also contemplated.

It is to be further understood with reference to FIGS. 12A–14B that the ability to open vent aperture (318) to atmospheric pressure at any time by removing the actuating user's finger therefrom contributes a safety feature to the overall design. It is contemplated that, during some uses, the suction in the tip of the device may aggressively engage and hold tissue proximate to that tip. In a case where the valving mechanisms provided with the device may stick in an actuated position, or when very rapid release of suction is desired, opening vent aperture (318) immediately shunts most all of the applied suction out that port to thereby allow for rapid release of engaged tissue at the applicator tip.

Figure 15:
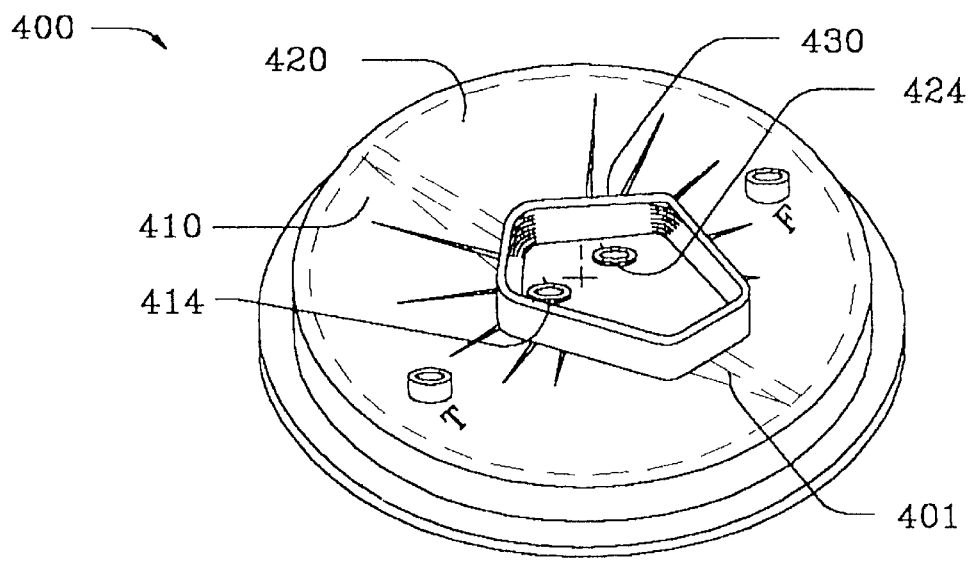
FIG. 15 is a perspective view of one preferred filling dispenser assembly used to fill the dispensing assembly of the supply device portion of the medical fluid applicator of FIG. 1.
Figure 16:
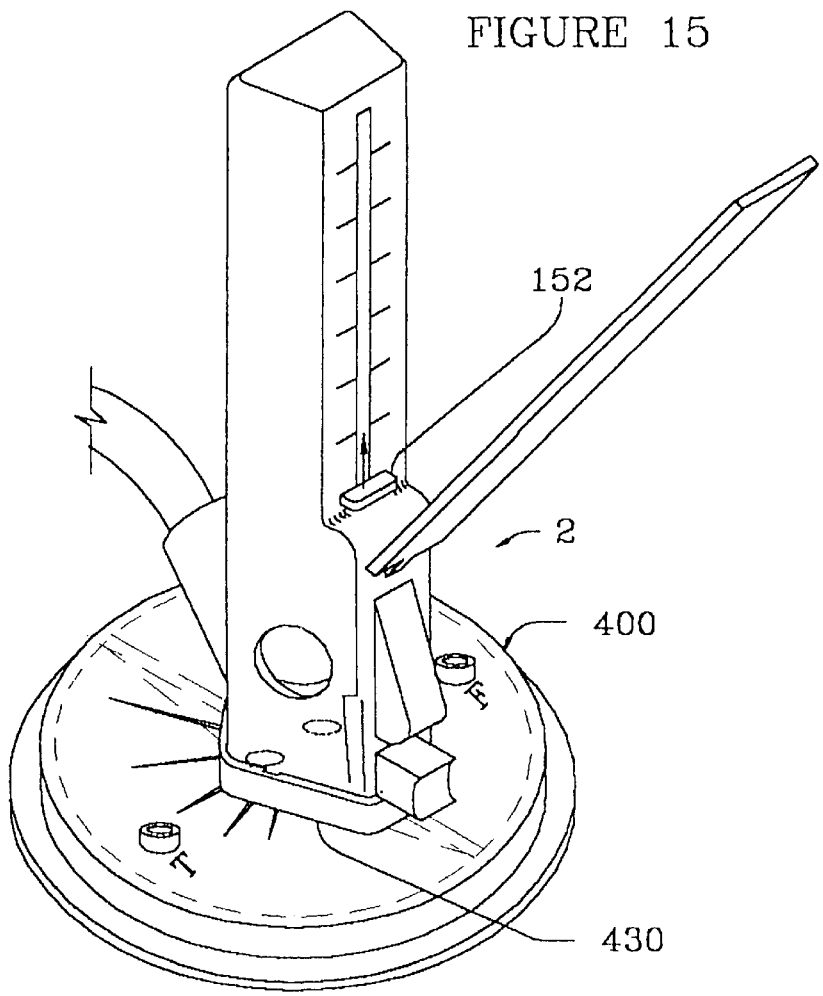
FIG. 16 is a perspective view of the dispenser assembly of FIG. 15 with the supply device portion of the medical fluid applicator of FIG. I engaged thereto in a predetermined filling orientation.
Figure 17A:
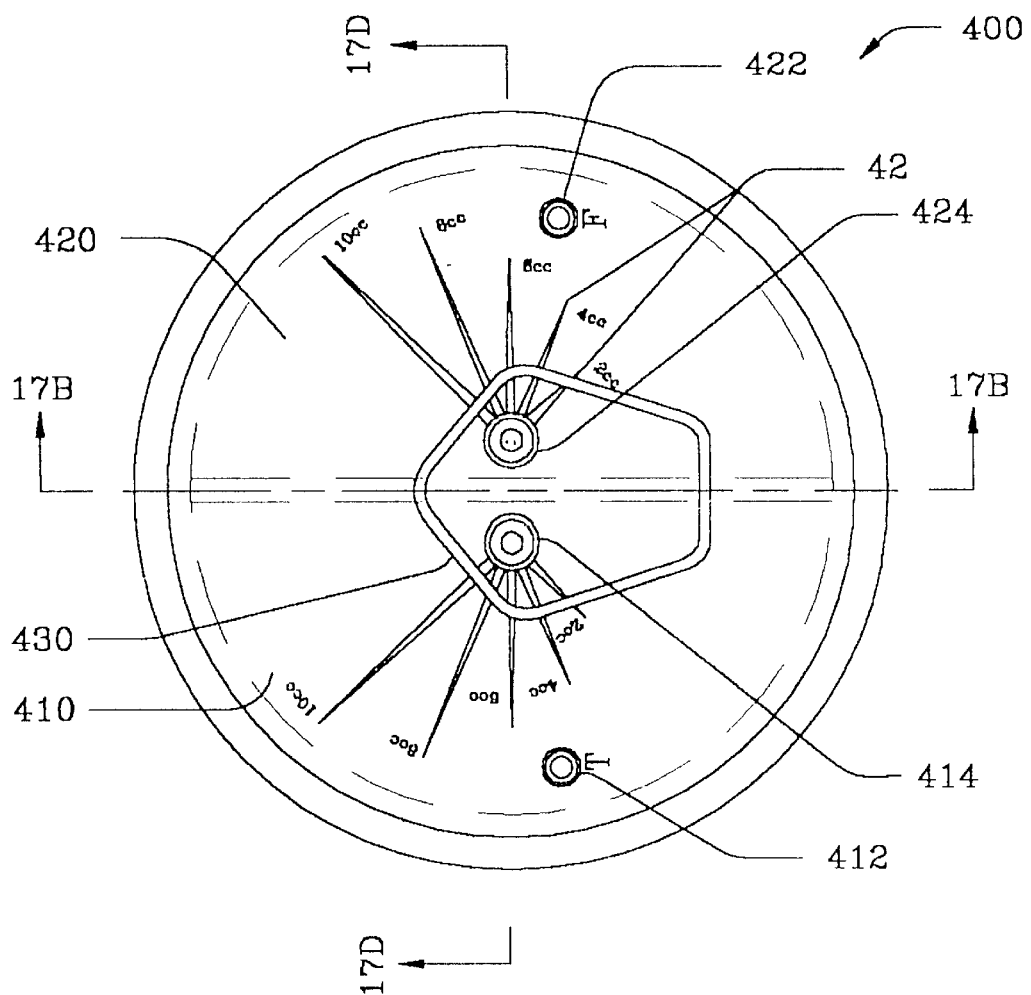
FIG. 17A is a top plan view of the filling dispenser assembly shown in FIG. 15.

In another aspect of the current invention, supply device portion (2) of medical fluid applicator is shown in FIGS. 15 and 16 during a filling operation using a beneficial design of filling dispenser. Further detail of the beneficial filling dispenser is shown for filling dispenser (400) in FIGS. 17A–E.

As shown generally in FIGS. 15 and 16, filling dispenser (400) includes first and second filling reservoirs (410,420) that are separated and isolated by a divider (401). Filling reservoirs (410,420) include dispenser filling ports (414, 424), respectively, which are adapted for use in filling the filling reservoirs with the desired fluids to be transferred to the supply device portion of the medical fluid applicator for delivery. In one variation, the filling reservoirs may be provided "pre-loaded" with liquid components, or in some cases dried components, of the desired fluid, in which case dispenser filling ports (414,424) may be used for additives such as catalysts, buffers, or other agents. Filling reservoirs (410,420) further include applicator filling ports (414,424), respectively, which are adapted to couple to supply ports of the supply device via keyed coupling (430).

As shown in overview in FIG. 16, keyed coupling (430) is adapted to engage supply device portion (2) such that the fluid reservoirs of the supply device portion are coupled to the applicator filling ports, and thus the filling reservoirs, in a predetermined orientation. In other words, only one, predetermined fluid reservoir of the supply device portion may be coupled to each filling reservoir of the filling dispenser. In the embodiment shown in FIG. 16, the actuating assembly is operated in a reverse mode for filling the fluid reservoirs. Tab (152) of the visual volume indicator is also adapted as a filling actuator, which may be manually withdrawn in the proximal direction to provide suction into the fluid reservoirs of the device and thus fill them with fluids from the coupled filling reservoirs.

FIGS. 17B depicts one of the filling reservoirs (420) which is filled at least partially with fluid (17), which may for example be one part of a two-part fluid, such as one of two parts which mix to form fluid (16) shown dispensed from medical fluid applicator (1) in FIG. 1. The portion of the supply device which couples with the applicator filling ports, which may be the supply ports respectively coupled to the fluid reservoirs as shown in FIG. 3, is shown in shadowed view in FIG. 17B. Here one supply port of the medical fluid applicator is shown coupled to applicator filling port (424) and is positioned within well (425) at the bottom of the respective filling reservoir (420). In this design, the efficiency in withdrawing a substantial portion of the fluid in the filling reservoirs is enhanced. FIGS. 17C–E show various views to enhance the understanding of the various features of filling dispenser (400) just described.

In the keyed coupling shown and described, the dispensing characteristics for each fluid reservoir may be specially adapted for the specific type of fluid which is contained in the predetermined filling reservoir to which it will couple. For example, each part of a two-part fluid may be contained in each filling reservoir. The two parts may be intended to mix in a particular ratio, such as in a ratio of one part of one fluid to two parts of the other. In this case, the fluid reservoirs of the supply device may have differing bore cross-sections such that one full actuation stroke constitutes one volumetric unit of fluid delivery from one fluid reservoir, and two volumetric unit of fluid delivery in the other. By keying the coupling between the supply device and the filling dispenser as provided in this variation, the proper fluid may always be filled into each fluid reservoir.

It is to be understood by one of ordinary skill that the present invention is not to be limited to specific types of fluids to be filled in the medical fluid applicator, and particularly in regards to the filling operation provided with the filling dispenser just described. For example, biologic and synthetic tissue adhesives, wound closure sealants, and various pharmacologic agents may be dispensed from the filling dispenser and subsequently applied in medical procedures with the medical fluid applicator of the present invention.

It is, however, believed that the various beneficial dispensing, suctioning, and clearing functions of the present invention present particularly useful benefits in the medical application of delivering of biologic or other adhesives to tissue surfaces. In this regard, "adhesive" is herein used throughout this disclosure to collectively describe substrates which are either useful literally as adhesives for adhering biological tissues, and/or which are useful as sealants or closure substrates used to seal spaces within the body, such as for wound closure procedures.

More particularly, it is further believed that delivery tissue adhesives or sealants which cure or coagulate relatively rapidly may present a particular need for the clearing feature provided with the current invention and described in detail above. The term "cure" and derivatives thereof is herein used throughout this disclosure to mean any mechanism giving rise to substantive physical change in the substrate which affects its mechanical and fluid flow properties, such as for example "coagulating", "congealing," or "cross-linking" mechanisms. Furthermore, such "quick" curing substrates often come in two-part form which, upon mixing, activates a rapid curing response.

Examples of such tissue adhesives or sealants the delivery of which may be enhanced by use of the clearing function just described are many. For example, several composite tissue adhesives ("CTA") have been described which may require retrograde clearing intermittently during a fluid delivery procedure. One example of a suitable CTA for use with the present delivery invention may be fibrin-based composites such as fibrin-collagen composites. Furthermore, polyethylene glycol (PEG) cross-linked composites, such as PEG-collagen or PEG-hyaluronic acid composites may be suitable. A further example of a two-part tissue adhesive is disclosed in EP 592 242 to Edwardson et al, wherein a fibrin monomer is coadministered with a buffer solution in a tissue sealant operation.

Other examples of suitable substrates for delivery with the current invention include certain classes of protein polymers which have biologic adhesive qualities, such as an amplified fibrinogen-like protein which is activated either by chemical cross-linking, such as with glutaraldehyde, or by enzymatic cross-linking such as with thrombin or Factor XIIA. Furthermore, plain plasma mixtures, as well as platelet concentrates, have been disclosed for tissue adhering procedures, and may rapidly form coagulums in delivery conduits during delivery procedures. Synthetic polymers such as cyanoacrylate adhesives or the like may also be used for tissue adhering or sealing procedures and which may cure in the delivery conduit such that suction withdrawal may be beneficial.

Still further, other fluids in addition to or in the alternative to tissue adhesives or sealants may have curing properties during delivery which would benefit by the clearing mode of operating the present inventive delivery device. For example, drug delivery fluids such as synthetic polymer substrates (PEG), bioerodable polymers, non-erodable polymeric excipients, hydrogels, cultured cells, or various other forms of pharmaceuticals (such as growth factor) or biologics may be delivered as a substrate which clogs a dispensing conduit during medical fluid delivery procedures.

Figure 18B:
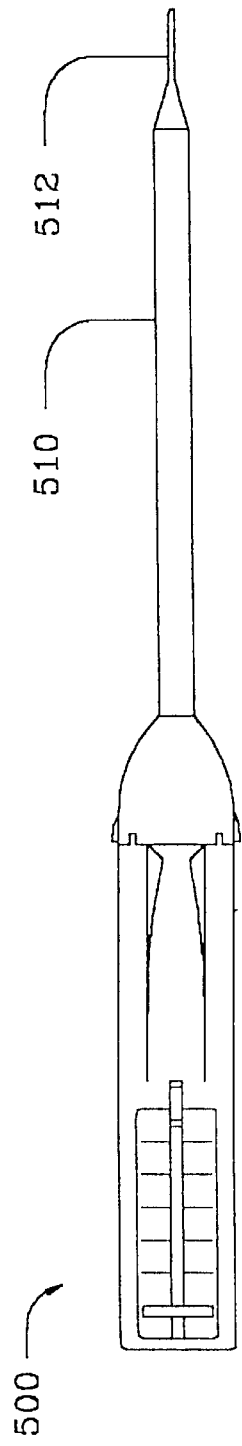
FIGS. 18A–C are side perspective, top perspective, and user end perspective views, respectively, of further actuating trigger and applicator tip variations adapted for moderately invasive surgery applications of the present invention.
Figure 18A:
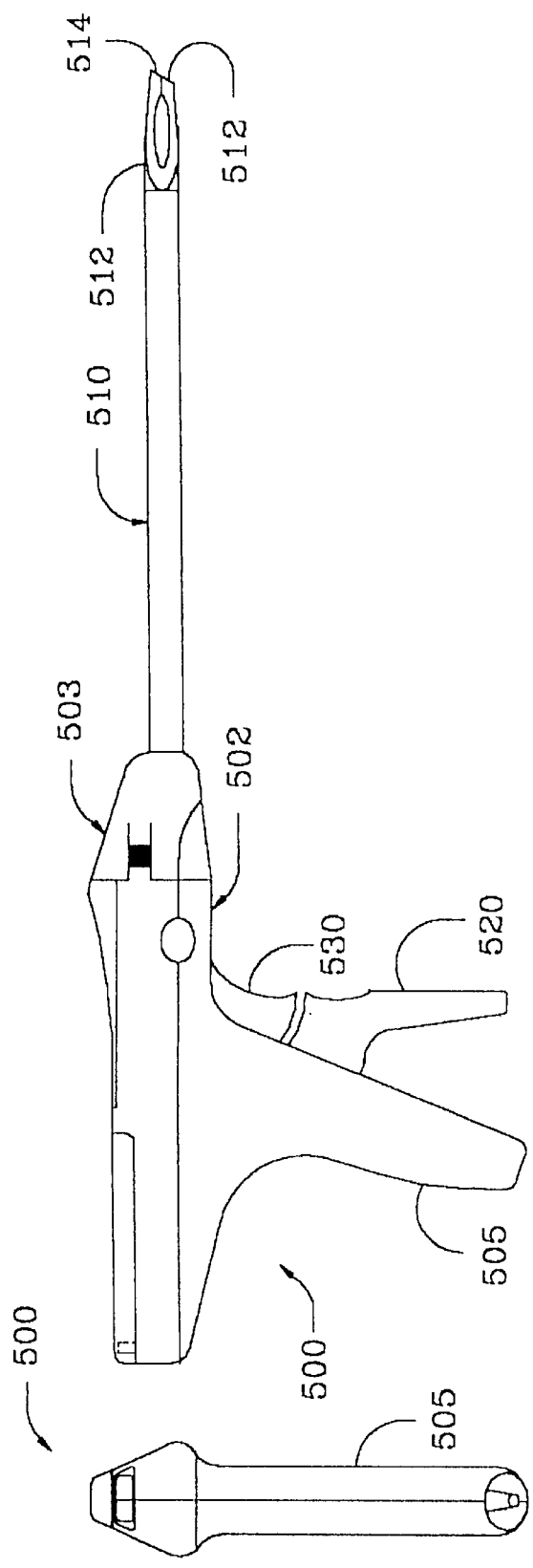
Figure 18C:
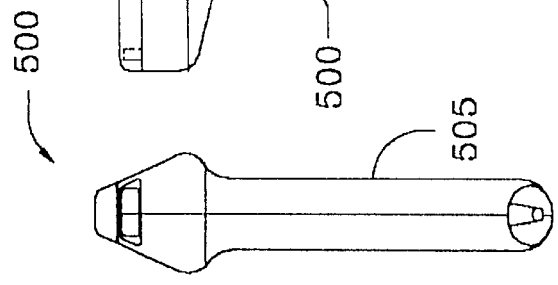
Figures 19A, 19B, 19C, 19D:
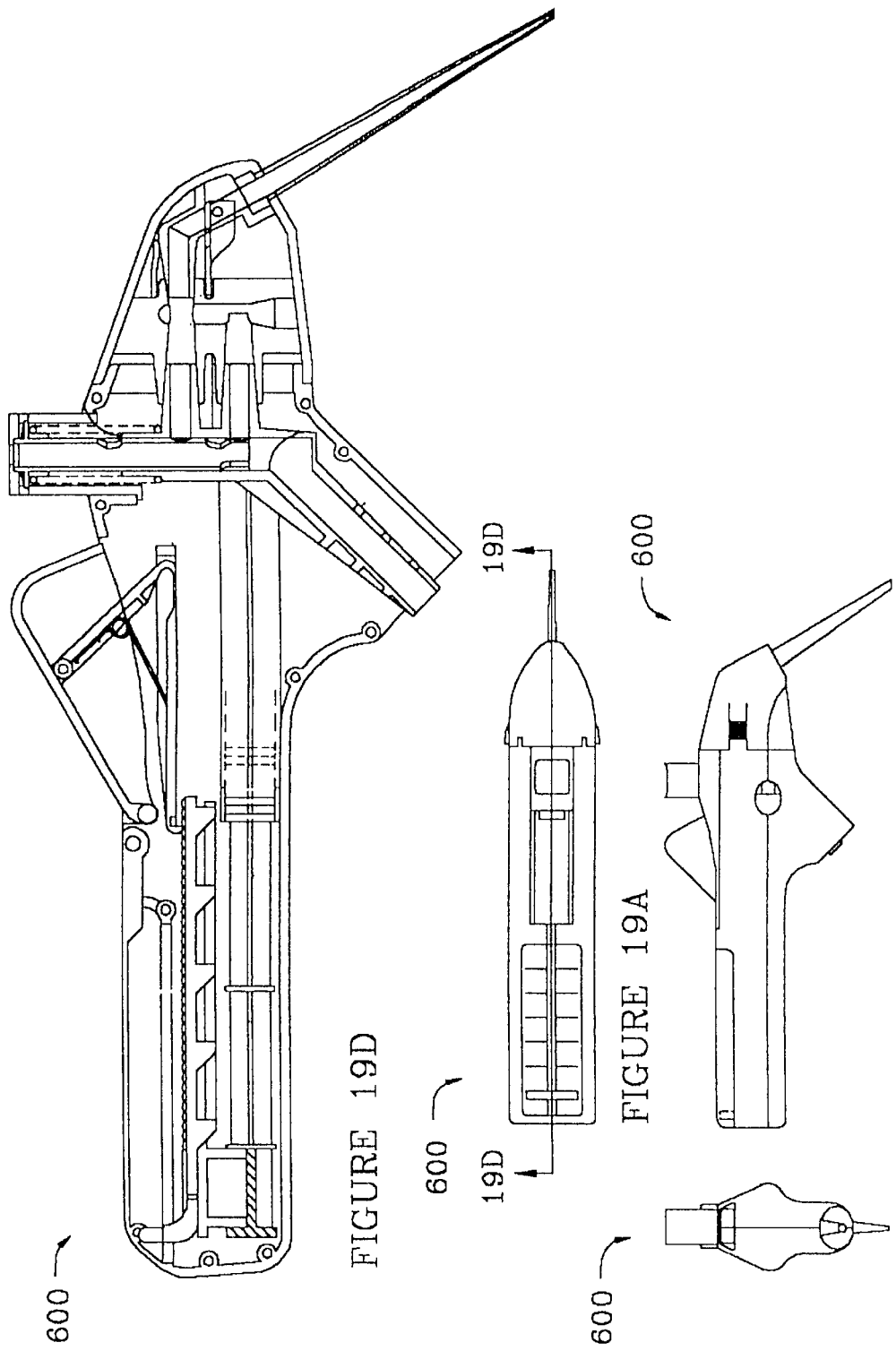

In addition to the broad field of substrates which may be suitable for use with the present invention, the present invention is also not limited to only the particular structural embodiments which are described in detail above. For example, FIGS. 18A–C show a further variation of both the supply device portion and the applicator portion of the medical fluid applicator invention. Furthermore, FIGS. 19–20C show another alternative variation for the applicator portion of the medical fluid applicator.

The medical fluid applicator (500) shown in overview in FIGS. 18A–C includes all of the internal componentry shown and described for the medical fluid applicator variations above, with some modifications to the dispensing and suction actuating assemblies in the supply device portion, and also to the applicator tip configuration of the applicator portion.

FIGS. 18A–B show applicator portion (503) of medical fluid applicator (500) to include an alternative variation for applicator tip (510) to that shown for the previous embodiments. Due to the elongated dimensions for applicator tip (510), it is believed that this variation has particularly beneficial application in moderately invasive surgical procedures for tissue adhesion or wound sealing, such as in less-invasive bypass procedures that are previously known and described in the art. It is to be appreciated by reference to FIGS. 18A–B in view of the previously shown and described embodiments that the internal structures of applicator portion (503) (not shown) are similar to that described for applicator portion (3) of those previous embodiments.

For example, applicator portion (503) includes a dispensing conduit that has a branched portion and a mixed portion, a suction conduit, a clearing conduit, and a shuttle valve such as those components previously described. However, in this variation, the branched portion of the dispensing conduit, the suction conduit, and the clearing conduit are all provided in an elongated form through the extended length of applicator tip (510). The mixed conduit component of the dispensing conduit, and also the distal portion of the shuttle valve which includes the dispensing and clearing valve portions, are preferably located in the distal region (512) of applicator tip (510). It is to be further understood that the suction conduit and the mixed portion of the dispensing conduit terminate distally in tip suction aperture (512) and tip dispensing aperture (524), respectively, as shown in FIG. 18A.

The actuating assembly for medical fluid applicator (500) is further shown in FIG. 18A, and includes a handle (505) which has an actuating trigger (520) coupled therewith. This variation is adapted for single handed use in actuating fluid dispensing. By gripping handle (505) and actuating trigger (520) in a user's hand, compressing the trigger against the handle actuates the dispensing assembly within the device to dispense fluids a predetermined incremental amount. Actuating trigger (520) includes a springbias and a full "stroke" range of motion which may be similar to the spring-bias and "stroke" described for the previous embodiments, such as with reference to FIG. 5. Furthermore, the coupling of actuating trigger (520) to the other components of the actuating assembly (not shown) may be similar to that described for the previous variation of FIG. 5, including the rack and pawl mechanism, and further including the audible and visual volume indicators previously described, as would be apparent to one of ordinary skill.

Also shown in FIG. 18A is a valve actuator (530) which is also coupled to handle (505) and is also adapted for single-handed use in a similar manner as actuating trigger (520). By depressing valve actuator (520) to various actuated positions relative to handle (505), a valve manifold (not shown) within the interior of the supply device portion (502) is adjusted to various positions to create a venting pathway, a suction pathway, or a clearing pathway. Furthermore, actuated motion of valve actuator (520) also selectively positions the shuttle valve component of the device (not shown) in order to close suction to the suction conduit and open communication for suction to the mixed portion of the dispensing conduit via the clearing conduit. The mechanisms provided by the valve manifold and the shuttle valve in this variation are the same as those shown and described for the previous embodiments, but for the coupling of valve actuator (520) to the manifold and the shuttle valve, which would be apparent to one of ordinary skill by this disclosure.

A further variation of the medical fluid applicator of the present invention is provided by reference to medical fluid applicator (600) in FIGS. 19A–20C. This variation includes all of the mechanical dispensing features, valving features, and actuating features of the previous embodiments, but includes only a single dispensing conduit (660) at the applicator tip (610) and omits the suction conduit feature of the previous embodiments. By this alternative variation, it is to be understood that the utility of applied suction for tissue preparation may be done in series with fluid dispensing through the same conduit, and need not be contemporaneous to fluid delivery through two, adjacent conduits as provided in the previous embodiments.

In this single conduit variation of the invention, it is contemplated that the device may be used during one particularly prolonged period for suction and in another prolonged period for dispensing. For this reason, it is less convenient to have a constant spring-bias to a rearward position for the shuttle valve, such that the valve must be manually actuated against the resting spring bias in order to close the dispensing pathway and open the suction/clearing pathway through the common conduit. Therefore, it is preferred in this variation to provide a detent locking mechanism (not shown) so that the shuttle valve may be temporarily locked into one of two positions for dispensing or clearing, respectively, such as the detent locking mechanism which is commonly used in opening and closing ball-point ink pens.

Figure 20A:
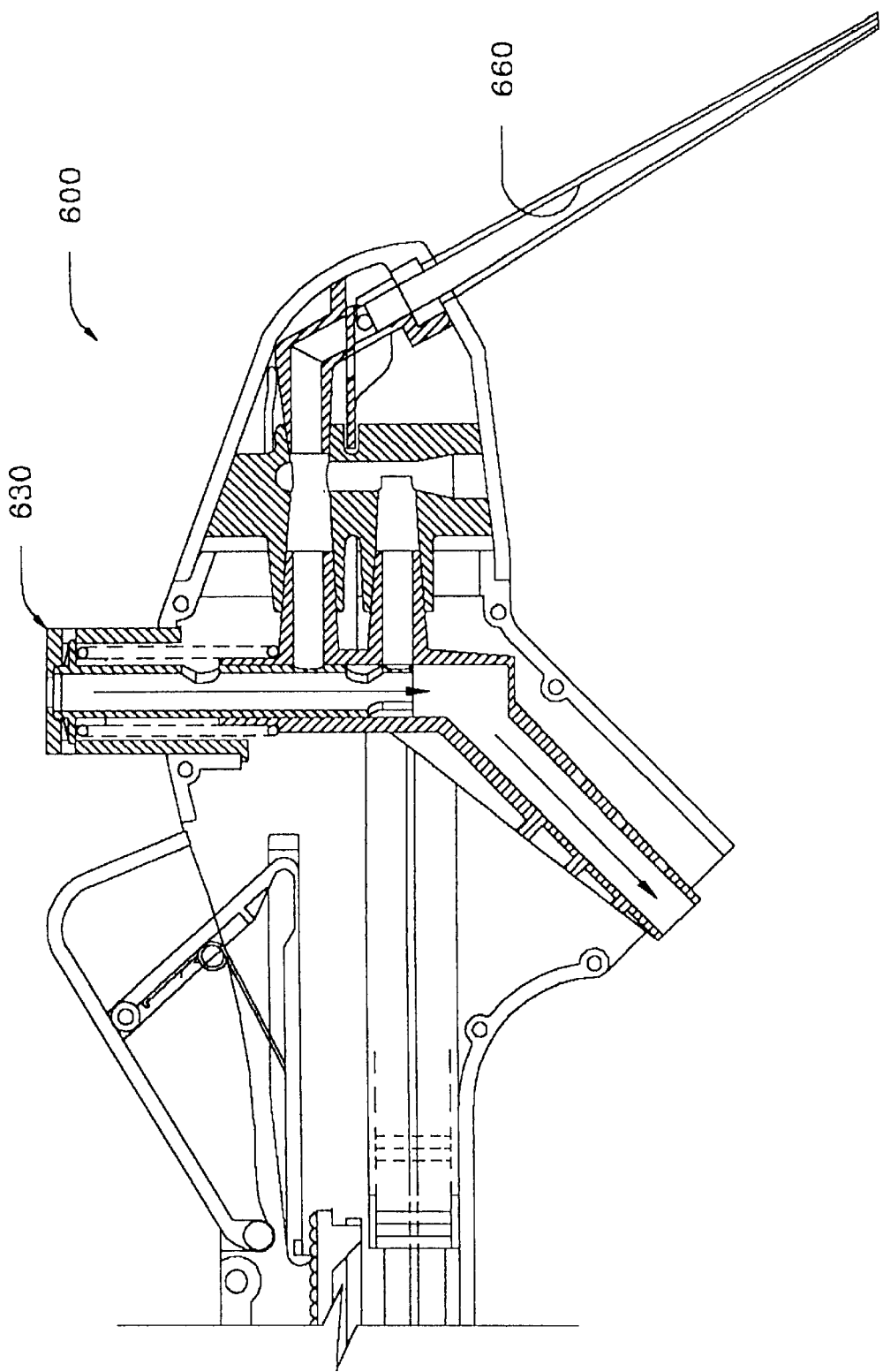
FIGS. 20A–C are exploded views of the applicator tip portion of the assembly shown in FIG. 19D, showing the valve manifold in sequential modes of operation in creating a vent pathway, a suction pathway, and a clearing pathway, respectively.
Figure 20B:
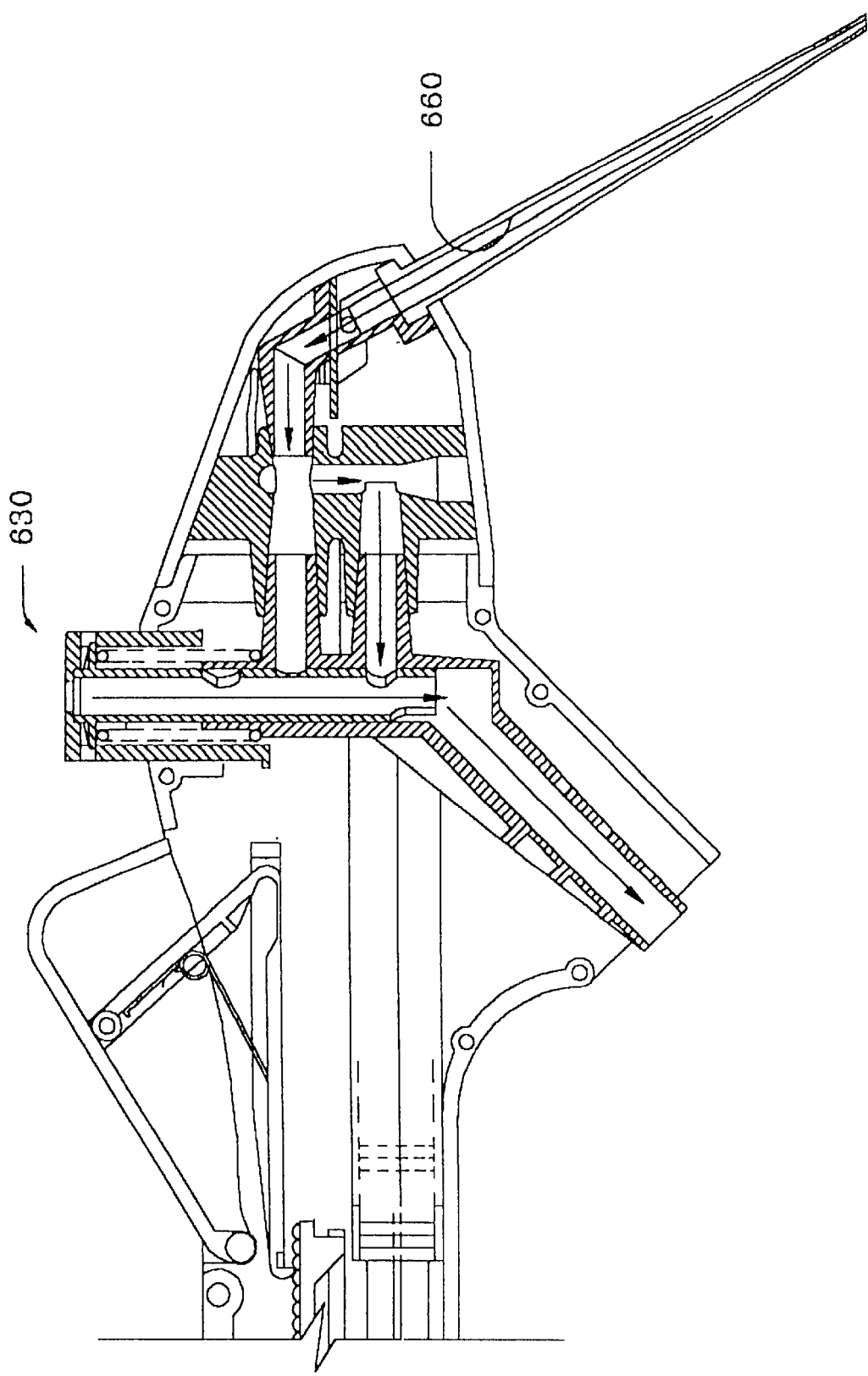
Figure 20C:
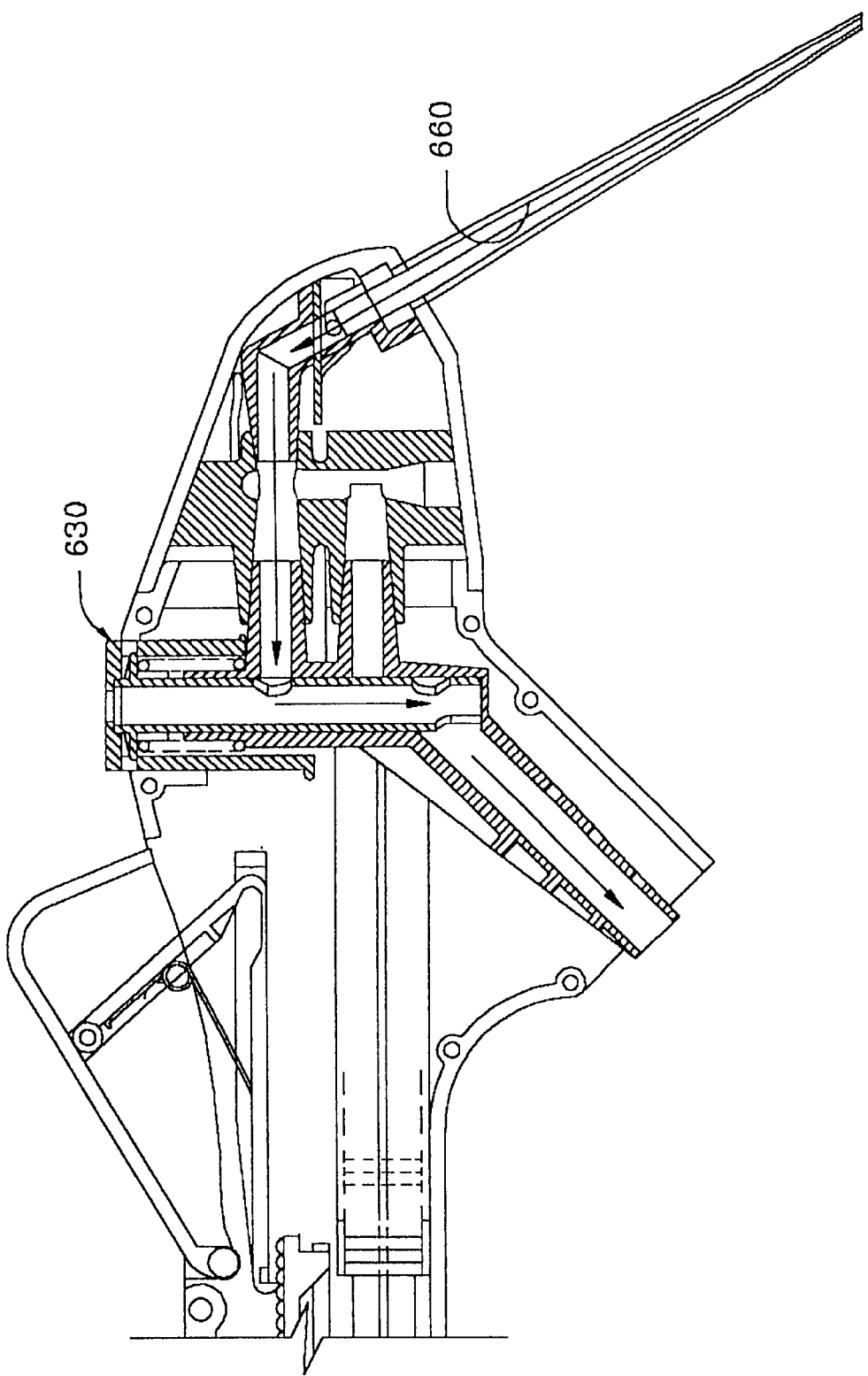
Figure 22:
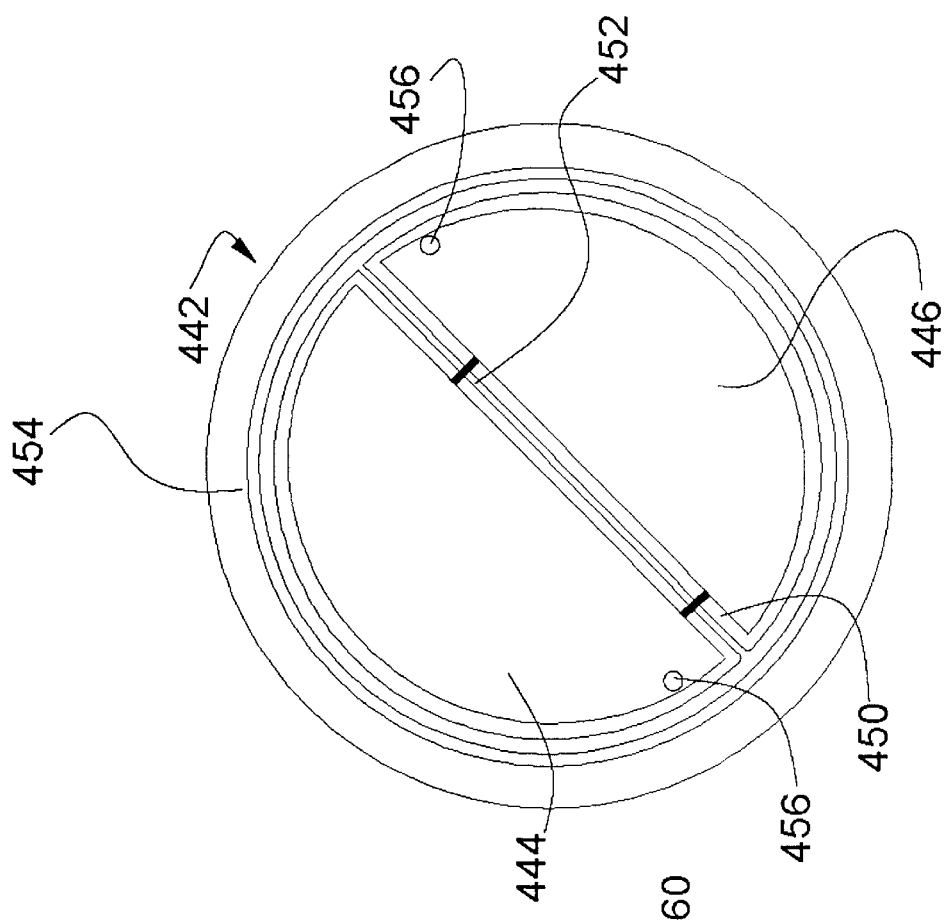
Figure 21:
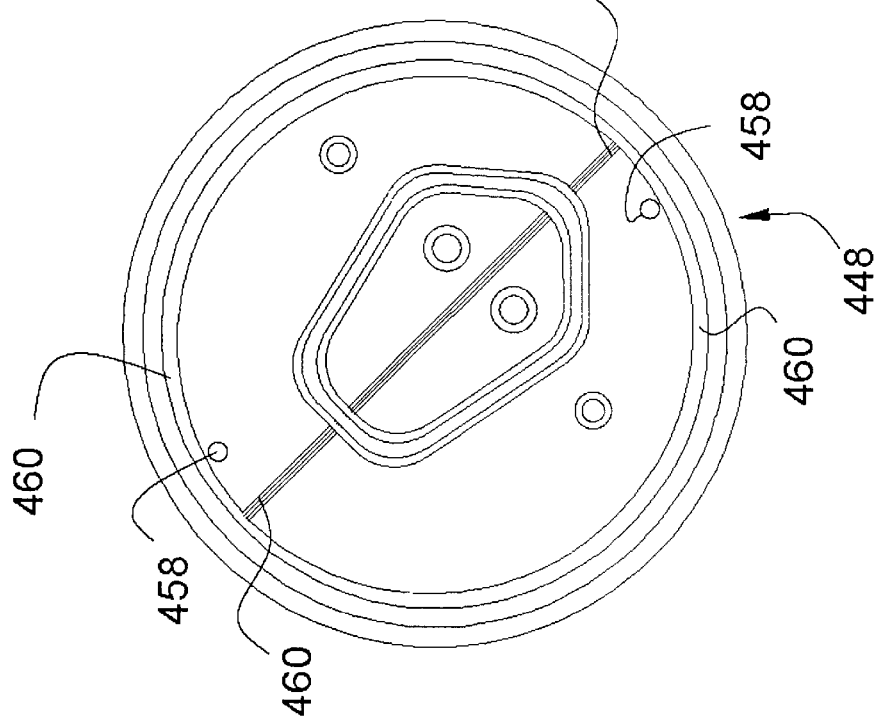

FIGS. 20A–C show various operating modes of this variation in a similar manner to FIGS. 12A–C in describing operation of the previous embodiment associated therewith. In FIG. 20A, valve manifold (630) is shown in a resting or venting position similar to that of FIG. 12A. In FIG. 20B, valve manifold (630) is shown actuated in a first suction position. In FIG. 20C, valve manifold (630) further shown in a second clearing position, wherein the distal mixed region of dispensing conduit (660) is retrogradedly cleared of its contents.

It should be understood by one of ordinary skill from the preceding disclosure that the present invention is broader than the particular embodiments described. Suitable alternatives to the particular described embodiments which are apparent to one of ordinary skill from this disclosure are considered to be included within the scope of the present invention.

What is claimed is:

1. A manually operable medical fluid applicator for dispensing mixed sealant on to a work surface, the applicator comprising:
    a) a fluid sealant dispensing pathway connecting with multiple sources of sealant components and including a mixing region where the sealant components can be mixed;
    b) a suction pathway connectable to a suction source and with the dispensing pathway; and
    c) a suction control valve operable to connect the suction pathway with the fluid dispensing pathway to apply suction to, and to remove undesired material from, the mixing region of the fluid sealant dispensing pathway.

2. A sealant applicator according to claim 1 comprising a valve to disconnect the fluid sealant dispensing pathway from the sealant component sources when the suction pathway is connected with the fluid dispensing pathway.

3. A sealant applicator according to claim 1 wherein the suction pathway comprises a suction dispensing aperture enabling suction to be applied to the work surface.

4. A sealant applicator according to claim 3 wherein the suction control valve is operable to apply suction to the suction dispensing aperture and to disconnect the suction dispensing aperture from the suction source when suction is applied to the fluid dispensing pathway.

5. A sealant applicator according to claim 1 wherein the fluid sealant dispensing pathway has a cross-sectional area which increases and does not decrease in a direction from a point of dispensing to a point of connection with the suction pathway to facilitate removal of undesired solids therefrom.

6. A handheld sealant applicator comprising:
    a) a housing with an applicator tip having a tip dispensing aperture;
    b) a fluid dispensing pathway within said housing comprising:
        i) at least two fluid reservoirs for two sealant components; and
        ii) a dispensing conduit leading from the fluid reservoirs to the tip dispensing aperture, the dispensing conduit having a distal portion including the dispensing aperture;
    c) a suction pathway connectable to a vacuum source;
    d) a clearing pathway connectable to the vacuum source via the suction pathway; and
    e) a control valve assembly capable of being coupled to the fluid dispensing pathway and to the clearing pathway and having a control valve having a valve member movable outside the fluid dispensing pathway from a first, dispensing position wherein the dispensing conduit is in fluid communication with the fluid reservoirs and is substantially isolated from the clearing pathway, to a second, clearing position wherein at least a distal portion of the dispensing conduit is substantially isolated from the fluid reservoirs and is in fluid communication with the clearing pathway.

7. A sealant applicator according to claim 6 comprising a manually operable dispensing actuator to dispense fluid contained in the fluid reservoirs through the dispensing conduit when the valve assembly is in the first dispensing position, wherein in the second, clearing position of the control valve assembly, the distal portion of the dispensing pathway is connectable with the vacuum source to clear the distal portion of its contents.

8. A sealant applicator according to claim 7 wherein one of said fluid reservoirs contains a first fluid, the other of said fluid reservoirs contains a second fluid and operation of the actuator causes said first and second fluids to flow distally from the fluid reservoirs and to form a mixture within the dispensing conduit.

9. A sealant applicator according to claim 8 wherein said first fluid is a fibrinogen-containing fluid and said second fluid contains an activator for coagulating said first fluid.

10. A sealant applicator according to claim 9 wherein the activator comprises thrombin.

11. A medical fluid applicator according to claim 6 wherein a biologically or pharmacologically active agent is contained in at least one of the fluid reservoirs.

12. A sealant applicator according to claim 6 wherein the dispensing conduit comprises:
    i) a branched portion having two branch conduits, each branch conduit being in fluid communication with one of the fluid reservoirs; and
    ii) a mixing portion having a mixing conduit which terminates distally in the tip dispensing aperture;
and wherein, when the control valve assembly is in the first dispensing position, the mixing conduit is isolated from the clearing pathway and is in fluid communication with the branch conduits so that fluid from the branch conduits is mixed in the mixing conduit prior to discharge through the tip dispensing aperture, and when the control valve assembly is in the second clearing position, the mixing conduit is in fluid communication with the clearing pathway and is isolated from the branch conduits.

13. A sealant according to claim 12 wherein the clearing pathway and the mixing conduit are coupled to form a continuously tapered bore with a distally reducing inner diameter.

14. A sealant applicator according to claim 12 wherein the valve assembly further comprises a clearing valve portion coupled to an inner lumen of the clearing pathway so that, in the first, dispensing position, the clearing valve portion substantially isolates the mixing conduit from the clearing pathway, and, in the second clearing position, the clearing valve portion couples the mixing conduit and the clearing pathway to allow for fluid communication therebetween.

15. A sealant applicator according to claim 14 wherein the control valve assembly further comprises two dispensing valve portions, each being coupled to an inner lumen of one of the branch conduits so that, in the first, dispensing position, the branch conduit is in fluid communication with the mixing conduit and, in the second, clearing position, the branch conduit is substantially isolated from the mixing conduit.

16. A sealant applicator according to claim 15
    wherein each branch conduit has a slotted portion to slidably receive one of the dispensing valve portions, the clearing pathway has a slotted portion to receive the clearing valve portion and each of the dispensing valve portions and the clearing valve portion has both a flow aperture and a closed portion
    wherein in the first, dispensing position, the flow aperture of each dispensing valve portion registers with the slotted portion of a branch conduit to allow flow therethrough, and the closed portion of the clearing valve portion registers with the slotted portion of the clearing pathway to substantially obstruct flow therethrough and wherein, in the second clearing position, the closed portion of each dispensing valve portion registers with the slotted portion of a branch conduit to substantially obstruct flow therethrough, and the flow aperture of the clearing valve portion registers with the slotted portion of the clearing pathway to allow flow therethrough.

17. A sealant applicator according to claim 6 further comprising:

f) a clearing conduit coupled to at least a distal portion of the dispensing conduit and adapted to form at least in part the clearing pathway;

g) a suction conduit adjacent the dispensing conduit and terminating at the applicator tip in a tip suction aperture;

h) a vacuum conduit adapted to couple to a vacuum source; and i) a valve manifold coupled to the clearing, suction, and vacuum conduits the valve manifold being adjustable from a first, suction position to a second, manifold clearing position;

wherein in the first, suction position the vacuum conduit is substantially isolated from the clearing conduit and is in fluid communication with the suction conduit to form a suction pathway and in the second, manifold clearing position the vacuum conduit is substantially isolated from the suction conduit and is in fluid communication with the clearing conduit to form the clearing pathway.

18. A sealant applicator according to claim 17 wherein the housing further comprises:

j) a body portion including the fluid reservoirs, the vacuum conduit, the valve manifold and a supply conduit fluidly coupling each fluid reservoir with one of two supply ports; and k) an applicator portion including the applicator tip, the dispensing conduit, the suction conduit, the clearing conduit, and the valve assembly;

wherein the dispensing conduit has a mixed portion and two branched channels extending proximally therefrom and terminates proximally in two proximal dispensing ports, the suction conduit terminates proximally in a proximal suction port, and the clearing conduit terminates proximally in a proximal clearing port and wherein the applicator portion is removably engageable with the body portion to bring the proximal dispensing ports into fluid communication with the supply ports and to couple the proximal suction port and the proximal clearing port with the valve manifold.

19. A sealant applicator according to claim 18 further comprising l) a valve housing housing the valve manifold and including a vacuum aperture in communication with the vacuum conduit, a suction aperture in communication with the suction conduit, and a clearing aperture in communication with the clearing conduit;

wherein the valve manifold further comprises a valve wall defining a valve chamber, the valve chamber communicating externally of the valve wall through a valve vacuum port, a valve suction port, and a valve clearing port, wherein, in the first suction position, the valve vacuum port and valve suction port are aligned with the vacuum and suction apertures, respectively, to form a suction pathway and the valve clearing port is out of alignment with the clearing aperture with the valve wall substantially isolating the clearing conduit from the suction pathway and wherein, in the second manifold clearing position, the valve vacuum port and valve clearing port are aligned with the vacuum and clearing apertures, respectively, to form the clearing pathway, the suction port being out of alignment with the suction conduit with the valve wall substantially isolating the suction aperture from the clearing pathway.

20. A sealant applicator according to claim 18 comprising a valve actuator which is coupled to both the valve assembly and the valve manifold, the valve actuator being adjustable from a first actuated position, wherein the valve assembly is in the first, dispensing position and the valve manifold is in the first, suction position, to a second actuated position, wherein the valve assembly is adjusted to the second clearing position and the valve manifold is adjusted to the second manifold clearing position.

21. A fluid adhesive applicator for dispensing a two-component fluid adhesive, the applicator comprising:

a) a dispensing aperture;

b) two fluid reservoirs respectively for the two fluid adhesive components;

c) a dispensing conduit capable of being in simultaneous fluid communication with the reservoirs and the dispensing aperture, the dispensing conduit having a mixing portion for simultaneously receiving and mixing the two fluids to form a mixture and a dispensing portion extending from the mixing portion to the dispensing aperture;

d) a manually operable dispensing actuator for effecting simultaneous flow of a fluid from each reservoir into the dispensing conduit; and e) a manually operable clearing actuator movable to apply a clearing force to clear undesired material from the dispensing conduit.

22. A fluid applicator according to claim 21 comprising a valve member movable to isolate the fluid reservoirs from the mixing portion, the valve member being operable by movement of the clearing actuator whereby the fluid reservoirs are isolated from the mixing portion when clearing of the dispensing conduit is effected.

23. A fluid applicator according to claim 21 wherein the fluid reservoirs comprise tubular chambers, each tubular chamber having a plunger slidable therein in response to manual operation of the dispensing actuator to discharge fluid in the chamber into the dispensing conduit.

24. A fluid applicator according to claim 21 comprising a clearing pathway communicable with a vacuum source wherein the clearing actuator comprises a shuttle valve to selectively couple the clearing pathway with the mixing portion of the dispensing conduit.

25. A fluid applicator according to claim 24 wherein the fluid reservoirs comprise syringes having plungers movable to discharge the fluids from the cylinders, wherein the applicator comprises a drive mechanism to translate operation of the dispensing actuator into movement of the plungers and wherein the housing houses the syringes, the vacuum valve and the drive mechanism.

26. A fluid applicator according to claim 21 having a suction aperture located adjacent the dispensing aperture and the applicator comprises a suction adapter connectable to a vacuum source to apply suction to the suction aperture.

27. A fluid applicator according to claim 26 comprising a suction valve operable to selectively apply suction from a vacuum source either to the suction aperture or to the dispensing conduit.

28. A fluid applicator according to claim 21 combination with a filling dispenser connectable with the fluid applicator and having separate volumes to contain separate supplies of the two fluids, the combination being operable to fill each of the fluid reservoirs with a predetermined one of the two fluids.

29. A fluid applicator according to claim 21 comprising a shuttle valve movable by the clearing actuator to a position isolating the fluid reservoirs from the mixing portion and comprising a clearing pathway communicable with a vacuum source wherein the shuttle valve selectively couples the clearing pathway with the mixing portion of the dispensing conduit when the fluid reservoirs are isolated from the mixing portion.

30. A fluid applicator according to claim 21 wherein the dispensing actuator is operable to dispense fluid from the reservoirs in discrete incremental volumes.

31. A fluid applicator according to claim 21 comprising an audible indicator responsive to operation of the dispensing actuator for providing an audible signal indicative of a cumulative volume of fluid dispensed from the applicator.

32. A fluid applicator according to claim 31 wherein the audible indicator generates an audible signal incrementally variable in either pitch or loudness according to the cumulative volume dispensed over a plurality of incrementally dispensed volumes.

33. A fluid applicator according to claim 21 comprising a toothed rack disposed adjacent the reservoirs and coupled with at least one reservoir to discharge fluid from the reservoir and a reciprocating pawl to move the toothed rack, a reciprocating pawl driven by the dispensing actuator to discharge the fluids from the reservoirs.

34. A fluid applicator according to claim 21 comprising a housing housing the fluid reservoirs and a dispensing conduit wherein the housing supports the dispensing aperture, the dispensing actuator and the clearing actuator to be accessible externally of the housing.

35. A fluid applicator according to claim 21 for dispensing a fibrin adhesive, wherein the two fluids comprise a fibrinogen component and a thrombin component in combination with supplies of the two fluids.

36. A medical fluid applicator for applying a medically useful fluid to a work surface, the applicator comprising:
   a) an elongated housing having a distal end and a proximal end and being receivable into one hand of the user;
   b) at least two reservoirs for components of a biological sealant attached to a branched dispensing pathway to dispense the components externally of the applicator;
   c) a dispensing cannula extending from the distal end of the applicator to dispense fluid from the at least two reservoirs;
   d) a manual actuator operable to apply manual force from the user to discharge fluid from at least two reservoirs to the dispensing cannula;
   e) a suction adapter intermediate the housing ends and projecting externally and traversely of the housing for connection with an external vacuum source; thereby permitting the user to operate the applicator with one hand and engage the suction adapter with said hand to help orient the applicator; and
   f) said branched dispensing pathway having two branches, each said pathway connected to at least one said reservoir, including the dispensing cannula, wherein a suction control valve communicates with the suction adapter downwardly through the housing between the two branches of the dispensing pathway.

37. The medical fluid adapter of claim 36 wherein the dispensing pathway is configured to mix the fluid components and discharge the mixture through the dispensing cannula when the manual actuator is operated to discharge fluid components from the reservoirs.

38. A medical fluid applicator to apply a two-component tissue sealant to a work surface, the applicator comprising:
   a) two syringes, one for each of two fluid components to be dispensed from the applicator, each syringe having a fluid reservoir and a plunger, the plunger being movable to vary the volume of the fluid reservoir;
   b) a reciprocally operable manual actuator to apply manual force from the user to discharge fluids from the reservoirs; and
   c) an actuator mechanism coupled with the manual actuator and the syringe plungers to translate force on the manual actuator into movement of the plungers in directions to discharge fluids from the reservoirs, wherein the actuator mechanism comprises:
      i) a toothed rack supported for travel outside the volumes of the fluid reservoirs the toothed rack having a series of teeth disposed along the rack in the direction of travel and being coupled with each plunger to move the plungers concurrently in their reservoirs and remaining coupled with the plungers throughout the plungers' travel; and
      ii) a rack advance mechanism to receive force from the manual actuator, and advance the rack and plungers in the fluid discharging direction, the rack advance mechanism having a reciprocally movable rack-engagement member engageable with successive ones of the teeth of the toothed rack to advance the toothed rack and plungers in a progressive manner;
   where in repeated operation of the manual actuator progressively discharges both fluid reservoirs at the same time.

39. A medical fluid applicator according to claim 38 wherein the syringes are disposed in side-by-side alignment, wherein the toothed rack is disposed alongside the syringe reservoirs and wherein the actuator mechanism has a mechanical advantage effective to apply an amplified manual force to the toothed rack.

40. A medical fluid applicator according to claim 38 wherein the rack advance mechanism includes a pawl cyclically engageable with the toothed rack to drive the rack in a direction to discharge fluid from the reservoirs, the pawl being movable in the discharge direction by the manual actuator.

41. A medical fluid applicator according to claim 40 wherein the manual actuator is movable transversely of the discharge direction and the rack advance mechanism comprises a pivoted lever to translate movement of the manual actuator into movement of the pawl.

42. A medical fluid applicator according to claim 41 comprising a housing housing the syringes, the rack and the rack advance mechanism.

43. A medical fluid applicator according to claim 38 comprising a decoupling structure to decouple the rack advance mechanism from the rack and a manually grippable rack member, wherein the rack member is coupled with the syringe plungers for retraction therewith whereby the rack and syringe plungers can be manually retracted by gripping the manually grippable rack member with the rack advance mechanism decoupled from the rack.

44. A biological fluid dispensing device, comprising:

a) a support member adapted to be held in the hand of a user;

b) plural reservoirs supported with respect to the support member, the plural reservoirs each defining an internal volume for containing a quantity of one of plural biological fluids to be dispensed;

c) plural output ports defined one for each reservoir;

d) a driver mechanically coupled to each reservoir and mounted for movement during a dispensing operation, the movement being within a range of driver positions with respect to the reservoir, and the driver cooperating with the reservoir to reduce the internal volume in response to advancement of the driver through the driver positions, and to drive the biological fluid through the output port;

e) an audible indicator coupled to the driver for emitting, in response to advancement of the driver position, an audible sound with an audible characteristic indicating the position of the driver and the corresponding magnitude of a volume of biological fluid contained within the internal volume; and f) plural conduits connecting one to each output port to deliver each fluid from a respective one of the reservoirs, wherein the conduits are configured and disposed to deliver the fluids to be mixed together.

45. A biological fluid dispensing device as claimed in claim 44, wherein the support member can be grasped by the hand of the user in a manner leaving at least one finger able to mechanically engage the driver to manually advance the driver to successive positions where the internal volume is successively reduced to drive the biological fluid through the output port.

46. A biological fluid dispensing device as claimed in claim 44, wherein the audible indicator comprises a first vibrating assembly having:

i) a striker; and ii) a plurality of vibrators, the vibrators being positioned, configured and dimensioned to emit an audible sound when struck by the striker;

wherein the driver is coupled to either the striker or the vibrators, movement of the driver within the range of positions causing relative movement between the striker and the vibrators, the movement causing the striker to sequentially strike the vibrators and cause the vibrators to emit the audible sound, wherein the audible sound has audio characteristics varying in accordance with the position of the striker, the variation in audio characteristics varying in accordance with a pattern which indicates to the user the magnitude of the internal volume, whereby the user can determine the volume of the biological fluid remaining in the device.

47. A biological fluid dispensing device as claimed in claim 46, wherein the audible indicator further comprises a second vibrating assembly having:

iii) a second striker; and iv) a second plurality of second vibrators, the second vibrators being positioned, configured and dimensioned to emit an audible sound when struck by the second striker;

wherein the driver is coupled to either the second striker or the second vibrators, movement of the driver within the range of positions causing relative movement between the second striker and the second vibrators, the movement causing the second striker to sequentially strike the second vibrators and cause the second vibrators to emit the audible sound, wherein the audible sound has audio characteristics varying in accordance with the position of the second striker, the variation in audio characteristics varying in accordance with a pattern which indicates to the user the magnitude of the internal volume, whereby the user can determine the volume of the biological fluid remaining in the device, and wherein the variation in audio characteristics of the first and second vibrating assemblies being a variation in pitch, the relationship between the pitch produced by the first vibrating system with respect to the pitch of the audible sound produced by the second vibrating assembly being an indication of the volume of biological fluid remaining in the device.

48. A biological fluid dispensing device as claimed in claim 47, wherein the first and second vibrating assemblies emit a series of sounds at discrete points corresponding to particular positions of the driver, successive sounds being of one pitch, several succeeding sounds being of a lower pitch, and so forth until the vibrators corresponding to the second subrange are struck by the strikers.

49. A biological fluid dispensing device as claimed in claim 48, wherein the audible sounds produced by the first and second vibrating assemblies are of different pitch in the positions between the positions corresponding to the first and second subranges, the difference in pitch generating an audio heterodyne varying from a high pitch to a low pitch as the internal volume is reduced in volume corresponding to movement from the first subrange of positions to the second subrange of positions.

50. A biological fluid dispensing device as claimed in claim 47, wherein the audible sounds produced by the first and second vibrating assemblies are of substantially identical high pitch in a first subrange of positions including the position where the internal volume is at a maximum, and of substantially identical low pitch in a second subrange of positions including the position where when the internal volume is at a minimum.

51. A biological fluid dispensing device as claimed in claim 50, wherein the audible sounds produced by the first and second vibrating assemblies change pitch at different positions between the positions corresponding to the first and second subranges.

52. A biological fluid dispensing device as claimed in claim 44, further comprising:

f) a second reservoir supported with respect to the support member, the second reservoir defining a second internal volume for containing a quantity of second biological fluid to be dispensed;

g) a second output port defined within the second reservoir; and h) a second audible indicator coupled to the driver for emitting in response to driver position a second audible sound with audible characteristics indicating the position of the driver and the corresponding magnitude of a volume of second biological fluid contained within the second internal volume;

wherein the first and second output ports are positioned, configured and dimensioned to communicate with a mixing chamber;

and wherein the driver is mechanically coupled to the second reservoir, the movement during the dispensing operation is within a range of driver positions with respect to the second reservoir, and the driver cooperates with the second reservoir to reduce the second internal volume in response to advancement of the driver through the driver positions, and to drive the second biological fluid through the second output port.

53. A biological fluid dispensing device as claimed in claim 44, wherein the output port is adapted to serve as an applicator nozzle for application of the biological fluid to a site to be treated with the biological fluid.

54. A biological fluid dispensing device as claimed in claim 44, wherein the output port is adapted to receive and engage an applicator nozzle for application of the biological fluid to a site to be treated with the biological fluid.

55. A biological fluid dispensing device as claimed in claim 44, wherein the audible indicator produces the audible sound in response to changes in the position of the driver.

56. A biological fluid dispensing device as claimed in claim 44, wherein the audible indicator applies acoustic energy to the support, causing the support to resonate.

57. A biological fluid dispensing device as claimed in claim 44, wherein the reservoir comprises a syringe cylinder and the driver comprises a syringe plunger.

58. A biological fluid dispensing device as claimed in claim 44, wherein the reservoir comprises a compressible bladder.

59. A handheld medical fluid applicator comprising:
 a) at least two reservoirs respectively for at least two fluids to be dispensed;
 b) a manual actuator to dispense the at least two fluids from the at least two reservoirs ;
 c plural conduits connecting one with each reservoir to deliver each fluid from a respective one of the reservoirs, wherein the conduits are configured and disposed to deliver the fluids to be mixed together; and
 c) an audible indicator providing an audible indication, as the at least two fluids are dispensed, of the cumulative volume dispensed of at least one of the fluids.

\* \* \* \* \*